(12) United States Patent
Cochran

(10) Patent No.: US 7,956,603 B2
(45) Date of Patent: Jun. 7, 2011

(54) SENSOR INDUCTORS, SENSORS FOR MONITORING MOVEMENTS AND POSITIONING, APPARATUS, SYSTEMS AND METHODS THEREFORE

(75) Inventor: William T. Cochran, Clermont, FL (US)

(73) Assignee: Medility LLC, Clermont, FL (US)

(*) Notice: Subject to any disclaimer, the term of this patent is extended or adjusted under 35 U.S.C. 154(b) by 458 days.

(21) Appl. No.: 12/214,201

(22) Filed: Jun. 16, 2008

(65) Prior Publication Data

US 2009/0309579 A1 Dec. 17, 2009

(51) Int. Cl.
*G01B 7/14* (2006.01)
*A61B 5/103* (2006.01)

(52) U.S. Cl. .................... 324/207.17; 600/595

(58) Field of Classification Search .................. None
See application file for complete search history.

(56) References Cited

U.S. PATENT DOCUMENTS

| | | |
|---|---|---|
| 2,408,524 A | 10/1946 | Mestas |
| 2,459,210 A | 1/1949 | Ashcraft |
| 3,020,527 A | 2/1962 | MacLaren |
| 3,268,845 A | 8/1966 | Whitmore |
| 3,483,861 A | 12/1969 | Tiep |
| 3,891,918 A | 6/1975 | Ellis |
| 4,308,872 A | 1/1982 | Watson |
| 4,373,534 A | 2/1983 | Watson |
| 4,408,159 A | 10/1983 | Prox |
| 4,777,962 A | 10/1988 | Watson |
| 4,807,640 A | 2/1989 | Watson |
| 4,813,435 A | 3/1989 | Arms |
| 4,817,625 A | 4/1989 | Miles |
| 4,865,038 A | 9/1989 | Rich |
| 5,036,275 A | 7/1991 | Munch |
| 5,069,221 A | 12/1991 | Smith |
| 5,090,410 A | 2/1992 | Saper |
| 5,159,935 A | 11/1992 | Sackner |
| 5,170,786 A | 12/1992 | Thomas |
| 5,209,230 A | 5/1993 | Swedlow |
| 5,216,364 A | 6/1993 | Ko |
| 5,226,417 A | 7/1993 | Swedlow |
| 5,329,932 A | 7/1994 | Yount |
| 5,331,968 A | 7/1994 | Williams |
| 5,497,147 A | 3/1996 | Arms |
| 5,642,043 A | 6/1997 | Ko |
| 5,760,577 A | 6/1998 | Shizuya |
| 5,777,467 A | 7/1998 | Arms |
| 5,879,292 A | 3/1999 | Sternberg |

(Continued)

OTHER PUBLICATIONS

Singer Instruments & Control, "SM Series LVDT," Catalog of Singer Instruments & Control, LTD. Year 2003, 1 page.

(Continued)

*Primary Examiner* — Jermele M Hollington
(74) *Attorney, Agent, or Firm* — Charles C. Krawczyk; Catherine A. Lewis

(57) ABSTRACT

A generally planar shaped inductor is disclosed that is particularly adaptable for use in motion or position sensors. One inductor can function as a signal input unit and another as a pick up unit in an arrangement wherein both inductors are placed in a generally parallel juxtaposition for flux flow there between. A movable armature is located between the inductors to control the amount of flux transmission between inductors. The position of the armature relative to the inductors controls the output signal generated by the pickup inductor that are adapted to be converted into indications of displacements.

3 Claims, 35 Drawing Sheets

U.S. PATENT DOCUMENTS

| | | |
|---|---|---|
| 5,902,250 A | 5/1999 | Verrier |
| 5,914,593 A | 6/1999 | Arms |
| 6,142,953 A | 11/2000 | Burton |
| 6,340,884 B1 | 1/2002 | Wolf |
| 6,356,075 B1 | 3/2002 | Shank |
| 6,413,225 B1 | 7/2002 | Sackner |
| 6,433,629 B2 | 8/2002 | Hamel |
| 6,461,307 B1 * | 10/2002 | Kristbjarnarson et al. ... 600/534 |
| 6,479,986 B1 | 11/2002 | Steinich |
| 6,529,127 B2 | 3/2003 | Townsend |
| 6,551,252 B2 | 4/2003 | Sackner |
| 6,622,567 B1 | 9/2003 | Hamel |
| 6,714,763 B2 | 3/2004 | Hamel |
| 6,781,366 B2 | 8/2004 | Hiramatsu |
| 6,810,753 B2 | 11/2004 | Valdevit |
| 6,810,754 B2 | 11/2004 | May |
| 6,845,256 B2 | 1/2005 | Chin |
| 6,926,679 B2 | 8/2005 | Friedrichs |
| 6,963,772 B2 | 11/2005 | Bloom |
| 7,039,449 B2 | 5/2006 | Al-Ali |
| 7,078,582 B2 | 7/2006 | Stebbings |
| 2007/0167879 A1 * | 7/2007 | Cochran ............. 600/595 |
| 2008/0033252 A1 * | 2/2008 | Estrella ............. 600/300 |
| 2009/0309578 A1 * | 12/2009 | Cochran ........... 324/207.16 |
| 2009/0309683 A1 * | 12/2009 | Cochran ............. 336/65 |

OTHER PUBLICATIONS

David S. Nyce, "The LVDT: A Simple and Accurate Position Sensor," Aug. 2005 Sensor Technology and Design, pp. 1-7.

* cited by examiner

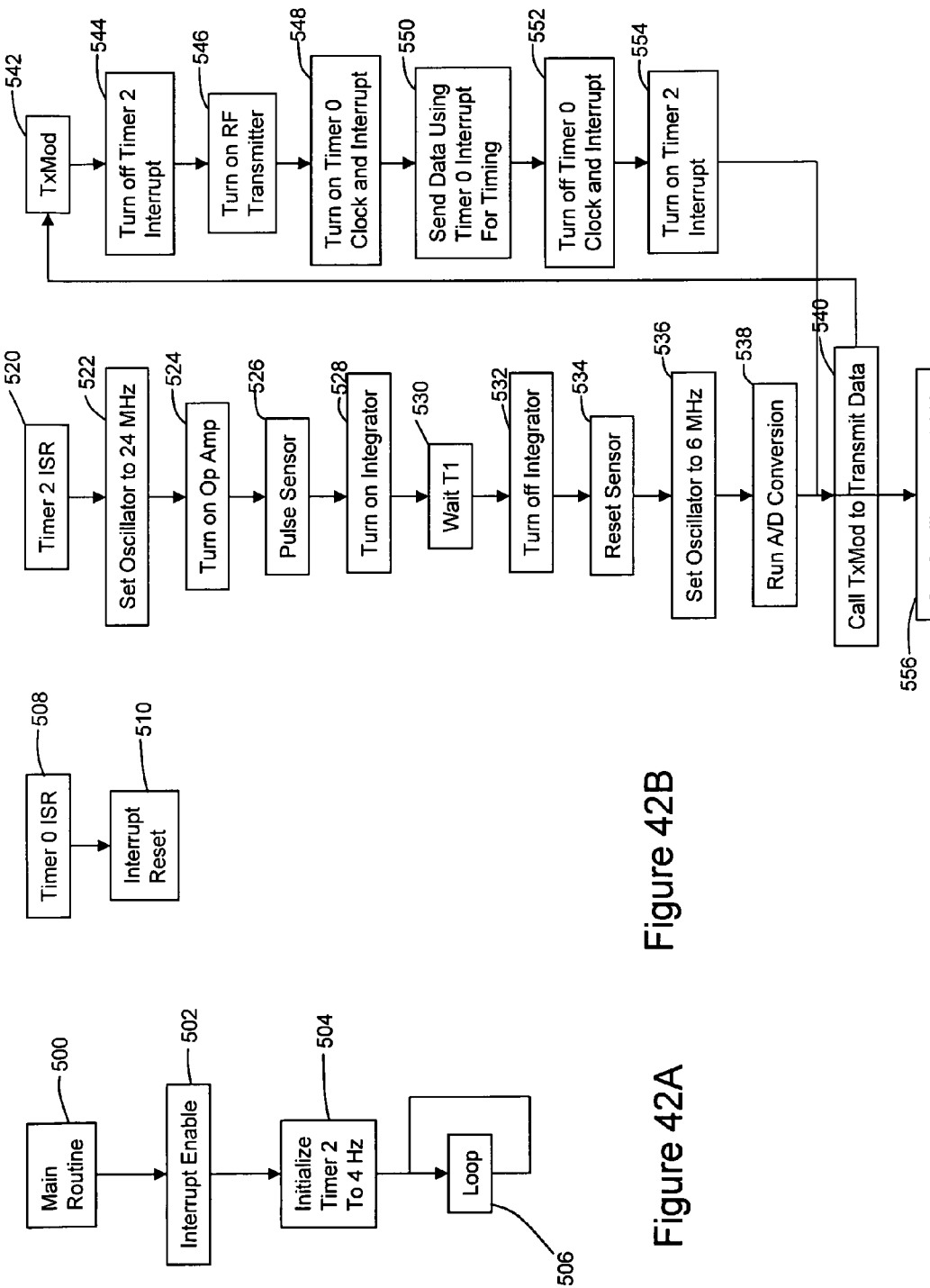

SENSOR INDUCTORS, SENSORS FOR MONITORING MOVEMENTS AND POSITIONING, APPARATUS, SYSTEMS AND METHODS THEREFORE

FIELD OF INVENTION

The present invention generally relates to sensor inductors, sensors, and sensors apparatus, systems and methods for monitoring movements in the form of deformations and displacements, and methods of using the sensor, to provide control, visual, and audible indications of the movements.

BACKGROUND OF THE INVENTION

With the ever increasing growth of automated systems used in various types of industrial and medical systems, there is a need for new and improved sensors and signal processing apparatus for monitoring movements related to force, torque, speed, acceleration, contraction, expansion, rotation, deformation, displacement, and the like. There is also a need to miniaturize such sensors to make measurements not otherwise possible with large and bulky sensors. For example, when monitoring the displacements of small or fragile items, or when monitoring deformations of flexible membranes such as skin, it is important that the sensor mass, its attachments, its electrical connections, and its operation, do not interfere with the movements being monitored to the extent that might otherwise significantly impact the accuracy of the measurements.

Such sensors and signal processing apparatus should preferably be subject to low manufacturing costs, not require high tolerance fits for moving parts, provide a sizable range of linear or tailored operation, and yet be relatively rugged.

Sensors of the prior art and inductors therefore for monitoring movements take the form of standard type transformers with multiple coils of turns of wires wrapped to extend longitudinally over a common axis, wherein the coils are being positioned adjacent to, or on top of, the other, in the form of a tubular unit. An armature extends along the axis into the tubular unit for movement therein relative to the coils and the magnetic flux from one coil flows along the armature to the other coil.

An example of a transformer type sensor is a linear variable differential transformer (LVDT) type sensor. A LVDT sensor is disclosed in the U.S. Pat. No. 5,216,364, issued on Jun. 1, 1993, entitled "Variable Transformer Position Sensor" that includes mechanical structures for use in automotive shock absorbers.

Miniaturized transformer type sensors based on the LVDT technology are disclosed in catalog publications by Micro-Epsilon entitled "Inductive Displacement Sensors and Linear Gaging Sensors," and by Singer Instruments and Control, Ltd. entitled "SM Series LVTD."

The U.S. Pat. No. 5,497,147, issued on Mar. 5, 1996, and entitled "Differential Variable Reluctance Transducer," and U.S. Pat. No. 5,777,467, issued on Jul. 7, 1998, and entitled "Miniaturized Displacement Transducer Assembly," and publication by MicroStrain entitled "Differential Variable Reluctance Transducer" (DVTR), disclose transformer type sensors The U.S. Pat. No. 3,891,918, issued on Jun. 24, 1975, and entitled "Linear Displacement Transducer Utilizing An Oscillator Whose Average Period Varies as a Linear Function of the Displacement," also includes a transformer type sensor.

Transformer type sensors are disclosed in the U.S. Pat. No. 5,216,364, and the Micro-Epsilon and the Singer publications, and in a publication by Analog Devices entitled "LVDT Signal Conditioner AD598 (Rev A)" and a publication by David S. Nyce of Revolution Sensor Company entitled "The LVDT a Simple and Accurate Position Sensor" dated August 2005.

In the field of medicine there is continual research and development for the design of new equipment for monitoring body changes to measure internal physiological properties, such as the chest for problems dealing with sleep apnea and the abdomen for pregnancy labors. The present solutions require the use of belt and/or vest type sensing arrangements. For sleep apnea the vests and belts surround the chest torso such as disclosed in many United States Patents, of which the following are sample patents: U.S. Pat. No. 5,329,932, issued Jul. 19, 1994, entitled "Method of and Apparatus for Monitoring Respiration and Conductive Composition Used Therewith," U.S. Pat. No. 6,142,953, issued Nov. 7, 2000, entitled "Respiratory Inductive Plethysmography Band Transducer," U.S. Pat. No. 6,413,225, issued Jul. 2, 2002, entitled "Quantitative Calibration of Breathing Monitors with Transducers Placed on Both Rib Cage and Abdomen," U.S. Pat. No. 6,461,307, issued Oct. 8, 2002, entitled "Disposable Sensor for Measuring Respiration," and U.S. Pat. No. 6,551,252, issued Apr. 22, 2003, entitled "Systems and Method for Ambulatory Monitoring of Physiological Signs." For pregnancy labors, the belts surround the abdomen such as disclosed in a Philips Medical Systems Nederland B. V. publication entitled "FM-2 Antepartum Portable Fetal Monitor." Each of these apparatus is bulky and as a result may be relatively uncomfortable to wear for extended periods of time, particularly if required to wear them overnight. Furthermore, although the apparatus may be portable, they are cumbersome, and may interfere with daily activities, and sleep.

There is a need to replace these massive and cumbersome belts and vest apparatus that encircle the body or cover large portions of the torso, and avoid short-term and long-term patient discomfort that may accompany their use. The apparatus should preferably be attached and worn with minimal discomfort, allowing the patient a significant amount of freedom of movement without impacting the tests underway. The apparatus should also preferably have a high degree of sensitivity to allow the equipment to detect small changes, particularly when testing infants, and be capable of continued operation as the patient changes positions.

The Q (quality factor) of a coil is defined as the ratio of the inductive reactance to the resistance of the transformer wire wound type coil at a given frequency. Q is a measure of the efficiency of storing energy; the higher the Q the more efficient the coil. To increase the Q in the abovementioned transformer type sensors, either the frequency applied to the sensors is to be increased, or the sensor inductive reactance increased (by the number of coil wire turns squared), or the sensor internal resistance is decreased. However, the miniaturization of the wire wound transformer type sensors do not scale well due to Q restraints. As the dimensions of these sensors are decreased, primarily by reducing the size of the wire, the internal resistance of the sensor coils increases significantly. It would be advantageous if the sensor design were not limited by Q restraints.

The use of commercial type strain gauges to measure deformations or the body was found unworkable in that their attachment of such strain gauges onto the body interfered with the movements of the part of the skin to which the gauges were attached rendering their use questionable.

In addition, it would advantageous if the monitoring apparatus was completely portable and adaptable for use over a wide variety of portions of the body for observing a wide variety of physiological problems.

Further it would be advantageous if the sensor could be subject to miniaturization for use with miniaturized monitoring circuitry, including radio, infrared, etc; for transmission of data to remote locations, with a readily detachable connection in between so that the low cost sensors can be discarded and the monitoring circuit reused.

SUMMARY OF THE INVENTION

The sensor inductor, sensors, system, apparatus and methods disclosed provide means for monitoring movements or deformations of objects. As used herein the term movement means, for example, alterations of form or shape, or positioning, or deformations, or displacements, of objects to be monitored, such as, but not limited to, locations, contractions, expansions, rotation, shape changes, volume changes, twisting, stretching, and ripple and wave actions. The loose mechanical tolerance between moving sensor parts enables the sensor to be used in monitoring movements of delicate items. The sensor is particularly adaptable to miniaturization, wherein the mass of the sensor, the loose mechanical tolerance between moving sensor parts, and the flexible electrical connections thereto, enables the sensor to be used in monitoring deformations, contraction and expansion, or other shape changes of flexible membranes such as experienced when monitoring skin, with insignificant interference with the movements. The movements may be elastic such as the contraction and expansion of skin, or plastic movements wherein residues of the changes remain.

In accordance with the invention, a magnetic field is adapted to be generated in which the flux lines flow generally normal to a surface, and the movement of the surface is adapted to be monitored by blocking or receiving some of the flux in a manner that varies with the movement of the surface.

An inductor or coil of the invention has a generally planar shape and is formed in a pattern or configuration, for example with multiple turns inwardly and with the turns diminishing in size, or serpentine, or regular, or irregular form. With the multiple turns inwardly pattern one end of the inductor is connected to a connection along an outside edge of the inductor and the other end is connected to an inner connector. The sensor inductor may take the form of a variety of shapes such as for example concentric circles, rectangles, triangles, serpentine, regular and irregular forms and can include bifilar arrangements. A sensor inductor may be formed along a sensor substrate such as a printed board, or contained within an epoxy coating substrate. The substrate can be rigid or flexible. Depending upon the sensor's use, the inductor may be formed on the item to be monitored as the sensor substrate.

An embodiment of a sensor of the invention includes at least two spaced apart sensor inductors or coils in general parallel juxtaposition and an armature is adapted to be positioned between the sensor inductors. The positioning of the sensor inductors and the armature is adapted to provide a measure of displacement there between. In an embodiment the armature is a thin flux-blocking metallic shield which can be of a variety of shapes to provide a desired sensor response.

In accordance to an embodiment of the invention the armature functions two coils are movable with respect to each other. One coil is adapted to receive excitation signals and the other coil is adapted to be used as an output coil. In response to the application of an excitation signal, magnetic flux flows from the excitation coil in a direction generally normal to the plane of the output coil wherein the positioning between the inductors is adapted to provide a measure of displacement there between.

The sensor inductor is essentially Q insensitive in its design, enabling the sensor to be manufactured in a variety of sizes to fit various monitoring needs, and is particularly adapted to miniaturization.

The sensor is adapted to be coupled to a monitoring circuit that is responsive to the changes in the response of the output of the sensor inductor as the magnetic flux changes, relative to the displacement between the sensor inductors and armature, to provide output signals that are indicative of the movements and/or locations.

Electrical pulses are applied to a sensor inductor and decaying electrical responses output from the other sensor inductor that are monitored and are a function of changes in the flux distribution between the sensor inductors. The monitoring circuit uses the time and magnitude characteristics of the output signal to providing an indication of sensed displacements and positions.

In accordance with an embodiment, the monitoring circuit selects a time slot between pulses to analyze the magnitudes of the sensor responses to provide an output indicative of the relative movements between the sensor inductors and the armature. Alternately the output signal can be integrated over the response of the excitation signal. In another embodiment the monitor circuit measures the time for the output signal to reach a predetermined level.

Various embodiments of the sensor of the invention have application to making measurement of movements with a wide variety of movable parts. The sensor is adapted to be connected in various arrangements wherein the outputs can be arranged to monitor movements relative to a zero reference point and provide directions of movements relative to the reference point, or provide very accurate indications of movements, or temperature insensitive indications of movements.

The sensor and sensing system of the invention is particularly adaptable for use in medicine in the measurement of deformation of skin such as contraction and expansion as a means for measuring local body volume changes, large volume changes, ripple or wave change action and shape changes when analyzing various internal body physiological properties, such as sleep apnea, baby crib death, pregnancy labor cramps, bladder incontinence, erectile dysfunction, muscle tension and contractions and limb movements. The sensor is also adapted to be attached to the body in arrays for providing multiple-directional analysis.

BRIEF DESCRIPTION OF THE FIGURES

FIGS. 42A-42F illustrate software diagrams for the operation to monitoring system.

DETAILED DESCRIPTION OF THE INVENTION

A copending U.S. patent application Ser. No. 11/321,162, filed on Dec. 29, 2005, entitled "Sensor for Monitoring Movements, Apparatus and Systems Therefore, and Method of Manufacturing and Use," for the same inventor as in the present application and owned by the same entity discloses a transformer type sensor that is Q insensitive and is adapted to miniaturization. The application also discloses a method of pulsing the transformer type sensor to provide signals for monitoring the relative displacement between the transformer coils and the armature. The application also discloses a power savings arrangement by operating with full power while making measurements and reduced power between measurements. This pending application is hereby incorporated by reference. A second copending patent application Ser. No. 11/906,851 was filed on Oct. 4, 2007, entitled "Bandage Type Sensor Arrangement and Carrier Assembly Therefore, and Method of Manufacture," for the same inventor as the present application and owned by the same entity. This pending application is hereby incorporated by reference.

This patent application is simultaneously filed on Jun. 16, 2008, the same day as the patent application Ser. No. 12/214, 200, entitled "Sensor Inductors, Sensors for Monitoring Movements and Positioning, Apparatus, Systems and Methods Therefore," and the patent application Ser. No. 12/214, 202, entitled "Sensor Inductors, Sensors for Monitoring Movements and Positioning, Apparatus, Systems and Methods Therefore," all for the same inventor as the present application and are owned by the same entity as the present application, and these applications are hereby incorporated by reference.

Detailed Description of the Invention

The sensor inductor, sensor, system, apparatus, and methods of the invention described herein are useful in monitoring movement positioning, and deformations in general, and have application for use with a wide variety of objects involved in industrial and commercial applications to measure, for example, relative positioning of parts, pressure, vibration, resonance, weight, expansion, and the like, and is also adapted to measure movements in a flexible membrane, such as skin for medical applications For medical purposes the sensor of the invention can be unobtrusively attached to the exterior of a body generally regardless of the location or shape, and measure changes in the skin due to movements, or changes in internal pressures, such as for monitoring: breathing, sleep apnea, prenatal symptoms, swelling, response to electrical stimulation and anesthesia. The size of the sensor can be made to be less than that of a postage stamp, and includes disposable sensor inductors and a re-usable monitoring circuitry.

Figure 1:
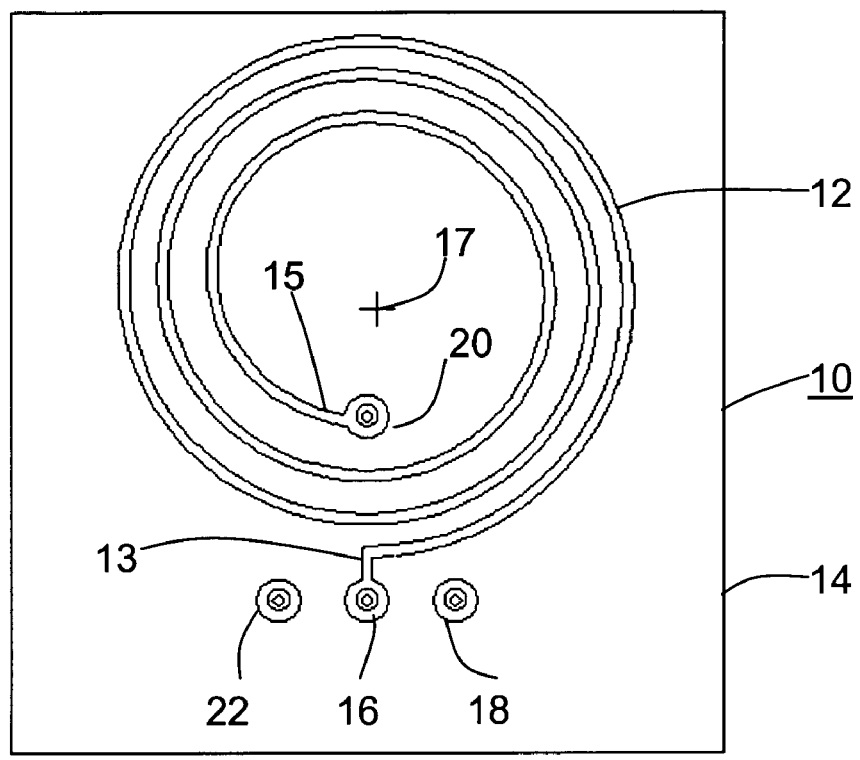
FIG. 1 illustrates an embodiment of a sensor inductor of the invention mounted on a substrate.
Figure 2:
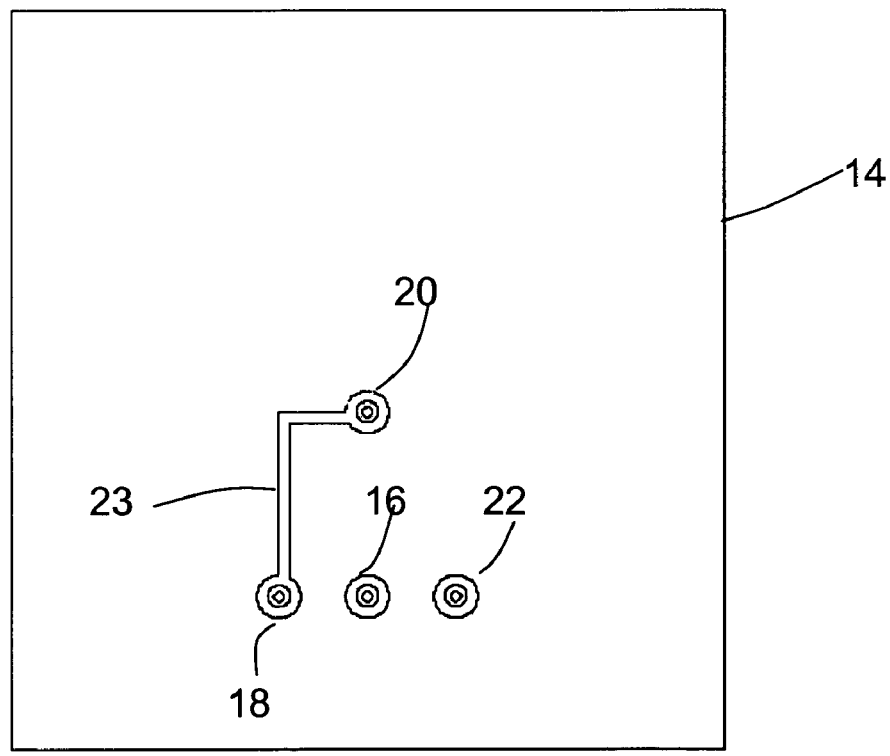
FIG. 2 illustrates a bottom view of FIG. 1.
Figure 3:
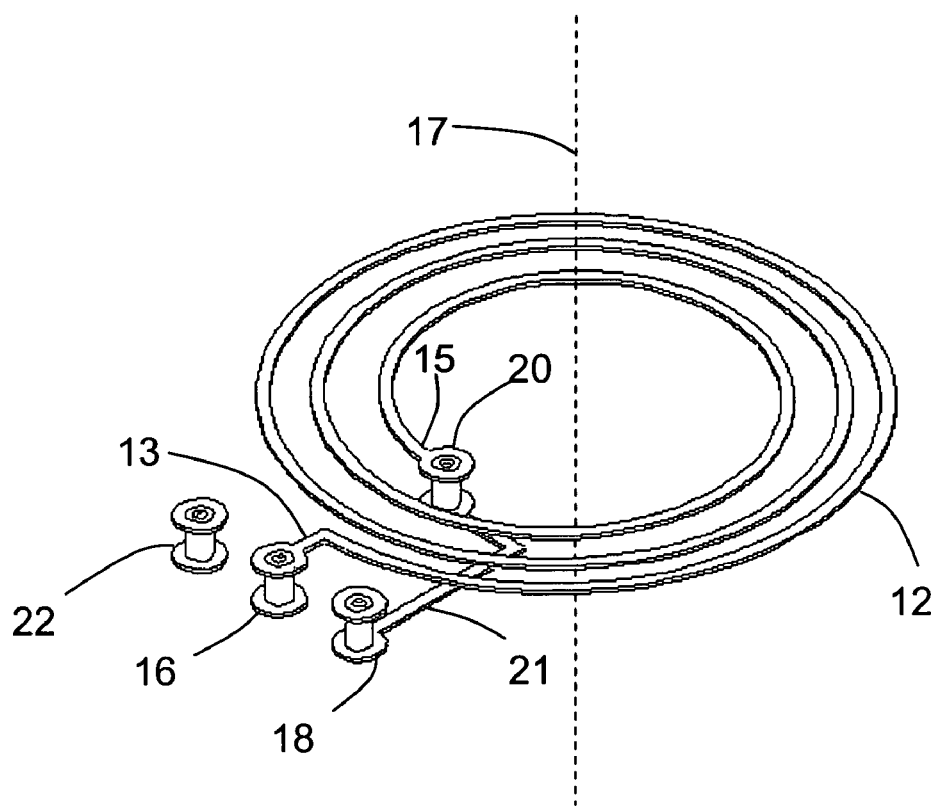
FIG. 3 is a perspective view of the sensor inductor of FIG. 1 without the substrate illustrating connections to terminals.
Figure 4:
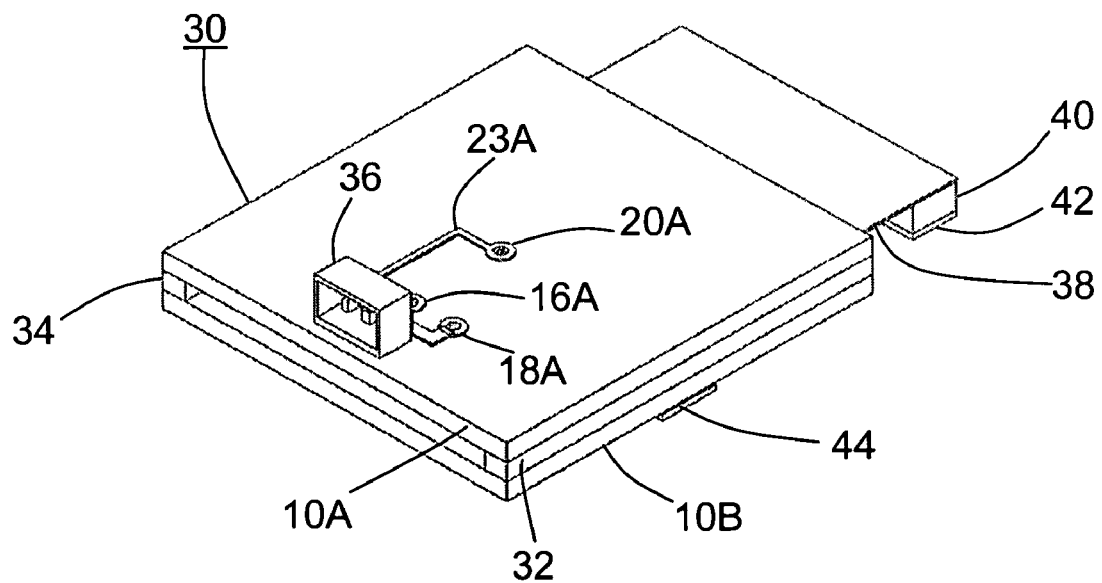
FIG. 4 is a perspective of an embodiment of the sensor of the invention including the sensor inductor of FIG. 1.
Figure 5:
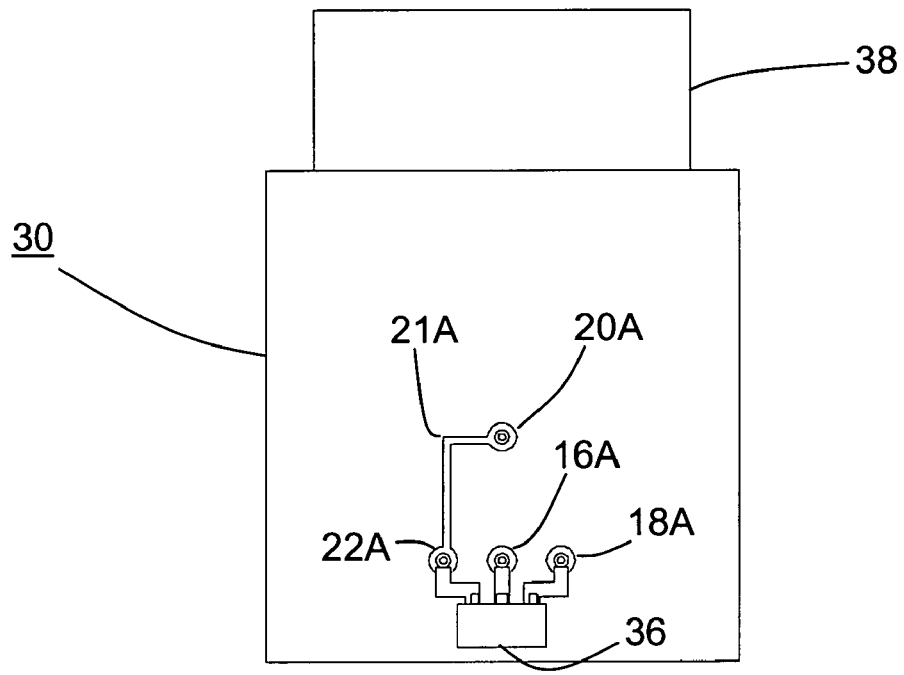
FIG. 5 is a top view of the sensor of the invention FIG. 4.
Figure 6:
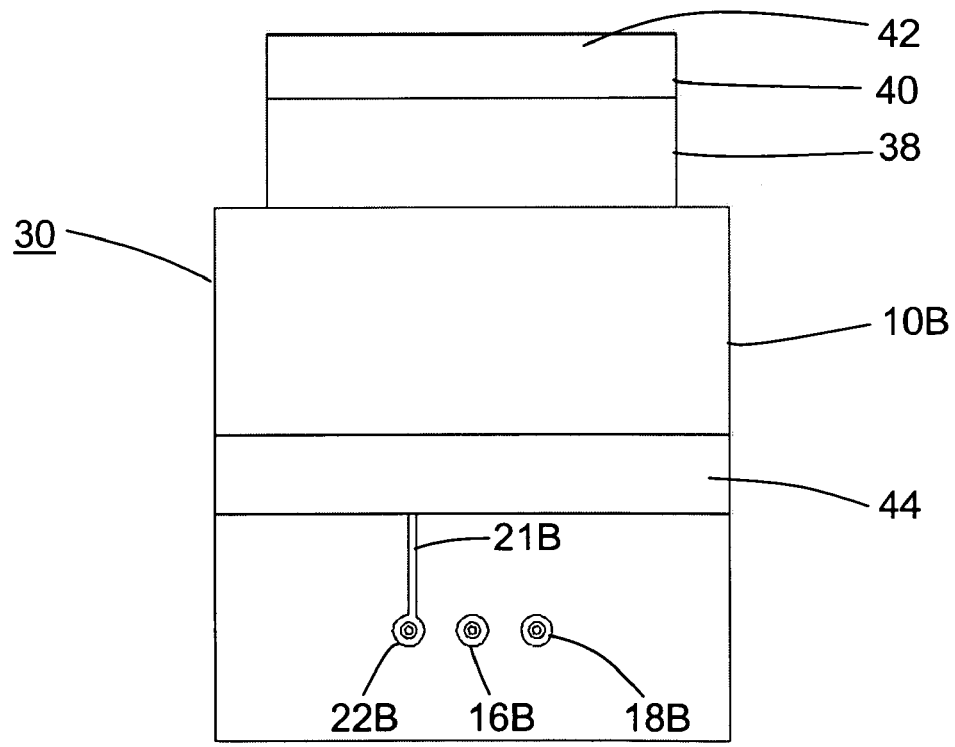
FIG. 6 is a bottom view of the sensor inductor of FIG. 4.
Figure 7:
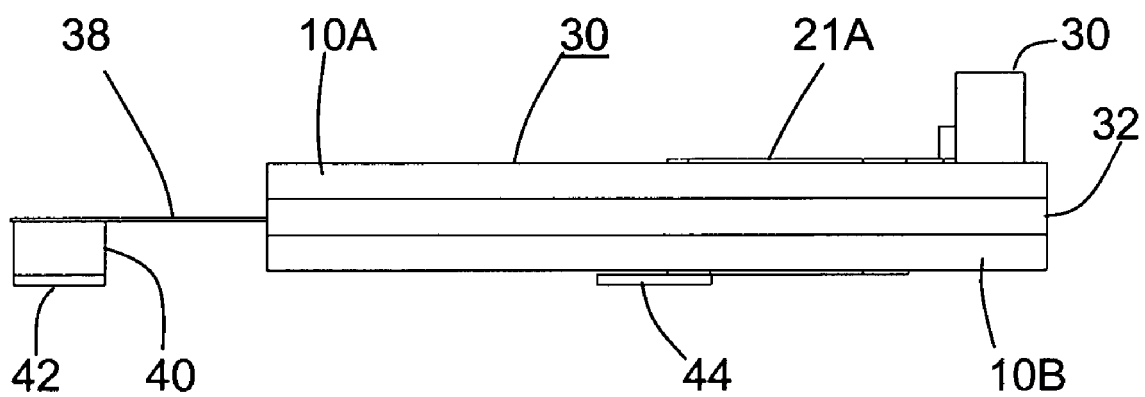
FIG. 7 is a side view of the sensor of FIG. 4.
Figure 8:
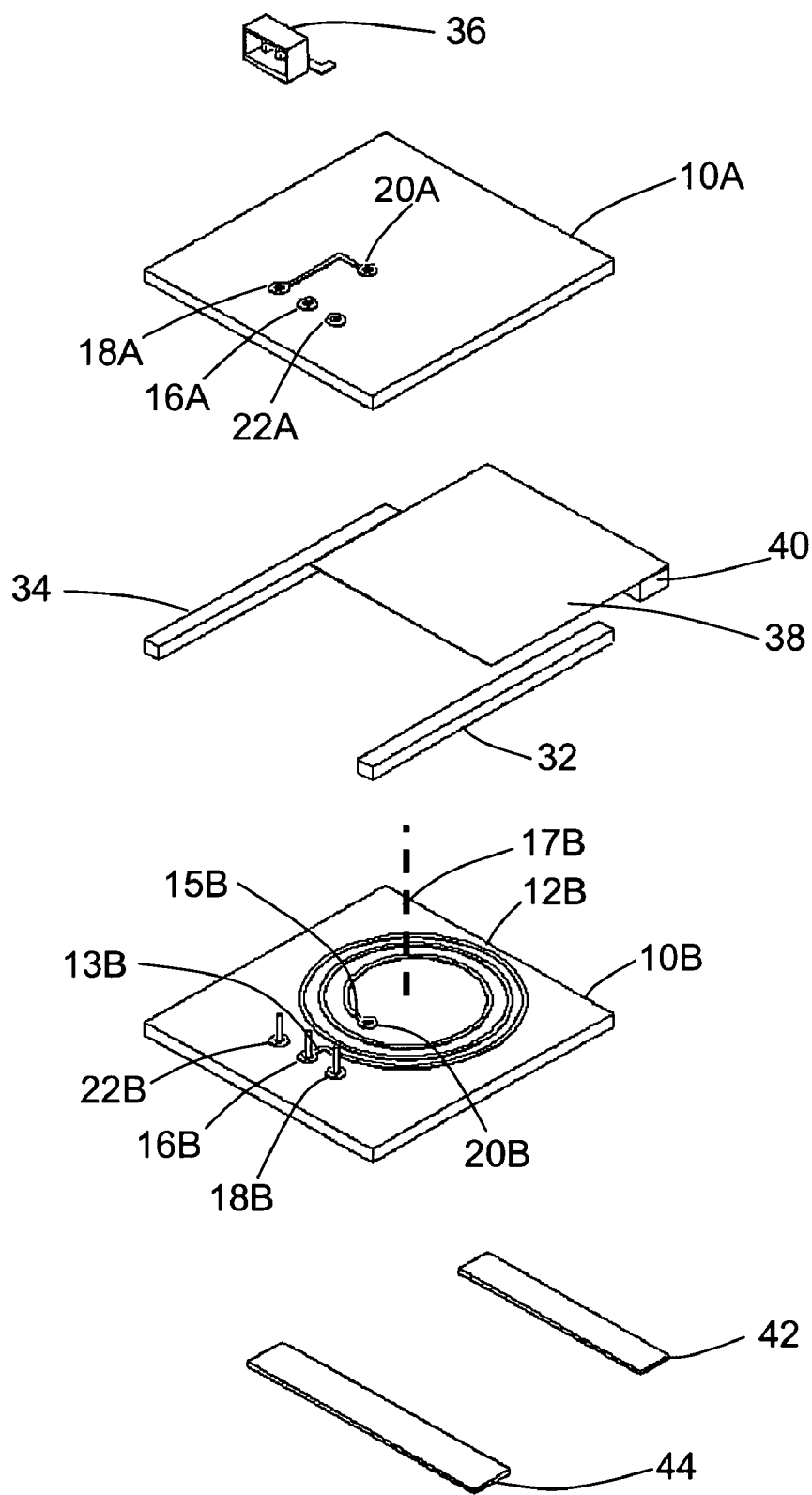
FIG. 8 is an exploded view of the sensor of FIG. 4.

As illustrated in FIGS. 1-3, the embodiment of the sensor inductor 10 of the invention includes a conductor or coil 12 mounted on, or formed on, or deposited on, or deposited within, a generally planar insulator, or semiconductor, or epoxy, sensor substrate 14. In the embodiment of FIGS. 1-3 the conductor 12 is wound with multiple turns inwardly about an axis 17 that extends generally normal or perpendicular to the substrate, with each turn diminishing in size or diameter. Generally planar, for the purposes of this invention, means a flat, cylindrical, or radial shape, and the like. The sensor substrate 14 can be the surface of the item to be monitored, or a separate substrate. The conductor 12 can be mounted or formed on printed circuit board type substrate by commercially well-known techniques. The inductor 10 can be encased within an epoxy substrate by dipping the inductor into an epoxy type liquid, or pouring the liquid over the inductor, and then allowing the epoxy liquid to harden. The substrate may be rigid, or flexible, provided the substrate is sufficiently rigid not to flex to the point to loosen, or break, the conductors 12. In situations where such sensor is to be permanently attached to a unit to be monitored, such as for industrial long term testing purposes, the inductor may be formed directly on the surface of the unit to function as the sensor substrate.

The size of the sensor inductor can vary depending on the desired design objectives. In the embodiment of FIGS. 1-3 the conductor 12 includes outer and inner ends 13 and 15 and is formed with multiple turns of a spiral circular configuration having turns of smaller diameters or size about the axis 17 (which is generally normal or perpendicular to the plane of substrate 14) as the conductor nears the center of the conductor (axis 17). For testing purposes a small sensor inductor was formed on a printed board sensor substrate one half inch square and one sixteenth inch thick with approximately twelve turns having a diameter less than a half inch. Although the substrate 14 is illustrated in FIGS. 1-3 with a rectangular form or pattern, it can be of any shape or configuration, including but not limited to, round or triangular, as dictated by the sensor's use. Although four terminals or connections 16-22 are disclosed, only three of the terminals 18-20 are needed for the use of the inductor alone. The terminal 16 is connected to the outer end 13 of the conductor 12 while the inner end 15 of the conductor is connected to the inner terminal 20. The terminal 20 is connected to the terminal 18 via a conductor 23. The connections of the conductor 12 to the terminals 18-20 is better illustrated in FIG. 3 with the substrate 14 removed.

The embodiment of the sensor 30 of the invention of FIGS. 4-9 includes a pair of separated sensor inductors 10A and 10B on sensor substrates are wound about the axis 17B and mounted in substantial parallel juxtaposition, separated by the separators 32 and 34. The terminals 16A-22A of sensor 10A are connected to a quick snap connector 36 for easy connection to and disconnection from a monitor circuit. An armature 38 is adapted to be positioned with a loose fit between the sensor inductors 10A and 10B. The armature 38 can be formed from commercially available METGLAS magnetic shielding film composed of a cobalt based alloy approximately 16 microns thick, available from Metglas Inc. The armature functions as a shield between the sensor inductors 10A and 10B for providing a means for varying the magnetic flux transmitted between sensor inductors as a function of the relative displacement between the armature 38 and the sensor inductors 10A and 10B. The use of Metglas is only exemplary, and other types of shielding material can be used. A mount 40 is attached to one end of the armature 38, the thickness of which is selected to approximate that of sensor inductor substrate 10B. An adhesive pad 42 is secured to the bottom of the mount 40 and another adhesive pad 44 is secured to the bottom of sensor inductor substrate 10B (as viewed in FIGS. 6 and 7). The adhesive pads 42 and 44 are a convent way of attaching the sensor 30 to the items for which movement is to be monitored. The terminals or connections 16A and 16B form a common connection to sensor inductor 10A and 10B, terminal or connection 18A provides the other connection to sensor 10A, and terminal or connection 22B provide the other connection to sensor inductor 10B.

Figure 9:
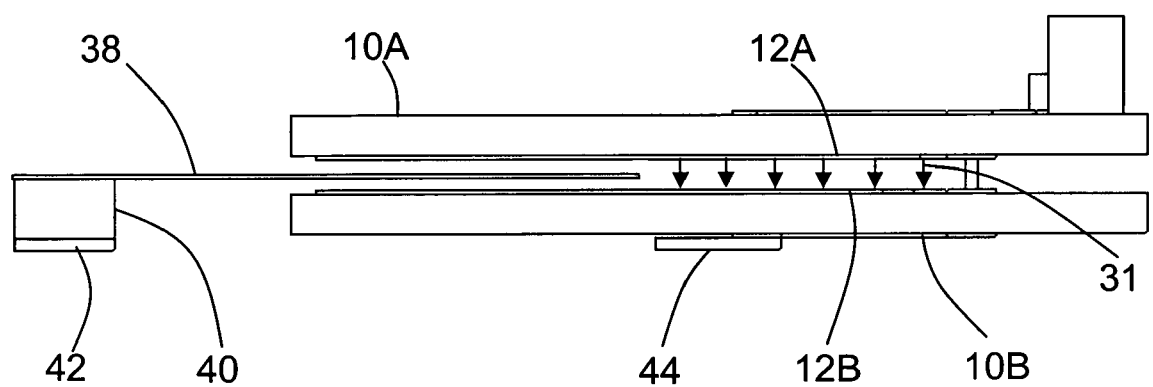
FIG. 9 is an illustration of the direction of magnetic flux flow between inductors or coils and the effect of a magnetic shield armature in blocking some of the flux.

The arrangement is such that either sensor inductor 10A or 10B can function as the sensor excitation unit while the other sensor inductor can function as the output or pick up unit. As illustrated in FIG. 9 (with the spacer 32 removed) the magnetic flux 31 flows from inductor 12A (selected to function as the excitation coil) along lines that are generally normal or perpendicular to the plane of the inductor 12B. With the shield or armature 38 fully extending between the sensor inductors 12A and 12B a minimum amount of flux generated by excitation inductor is transmitted to the other inductor. As the armature 38 is withdrawn (as illustrated in FIG. 9) the amount of flux transmitted between the inductors increases. Hence the sensor provides a signal amplitude at the output coil that is an inverse function of the displacement of the armature 38 within the sensor (relative to the inductors 12A and 12B). This flow of magnetic flux of FIG. 9 is from one coil generally normal or perpendicular to the other coil and armature wherein this arrangement contrasts to the flux flow in conventional coils of the prior art sensors wherein the magnetic flux flows along parallel to the armature. The armature, when functioning as a magnetic shield, decreases the magnetic flux flow the further the armature is inserted in between the coils, in contrast where the magnetic flow in conventional sensor coils is enhanced as the armature is further inserted into the coils. Although the coils 12A and 12B are illustrated in FIG. 9 in juxtaposition one over the other on parallel planes, it should be understood the arrangement is operable with the coils askew and flux lines less than perpendicular to the planes of the coils, or the coils are not exactly positioned one over the other, but with lower efficiency, hence described herein as being generally parallel, generally perpendicular or generally normal, and in general juxtaposition. Further, although the coils 12A and 12B are illustrated as having the same configuration, the shape or pattern of the coils can differ from each other, as with the use of the examples of patterns of FIGS. 12-14, or other regular or irregular shaped patterns, as the sensor design dictates.

Figure 10:
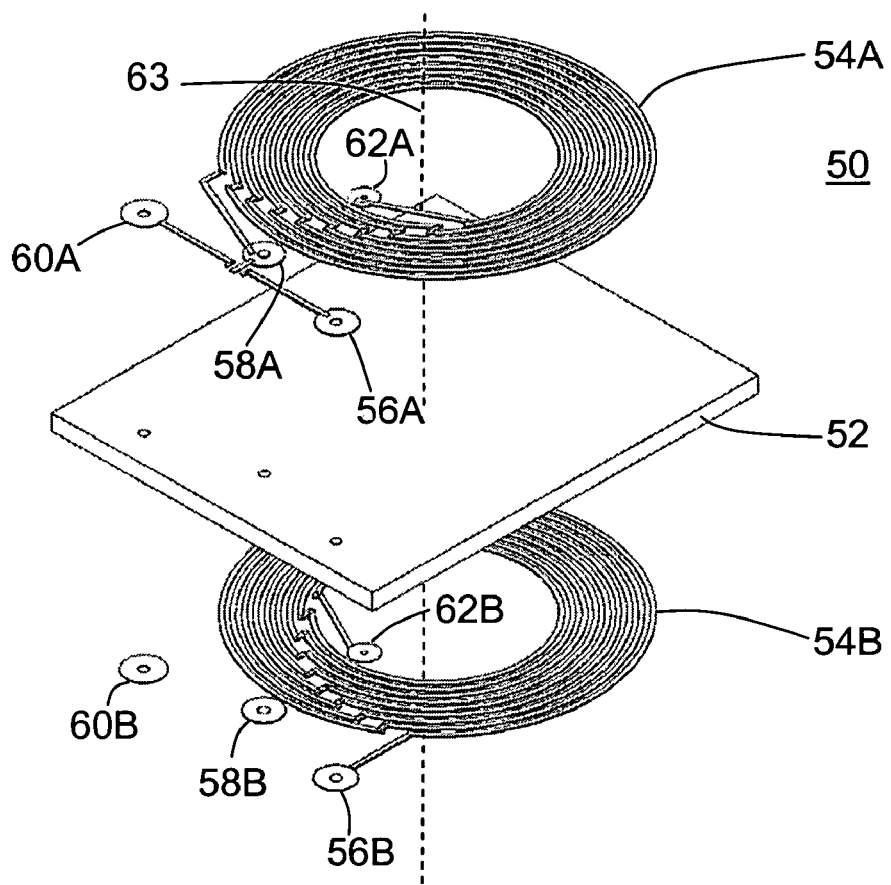
FIG. 10 is an exploded view of another embodiment of the sensor inductor of the invention including an inductor or coil on both sides of the substrate.
Figure 11:
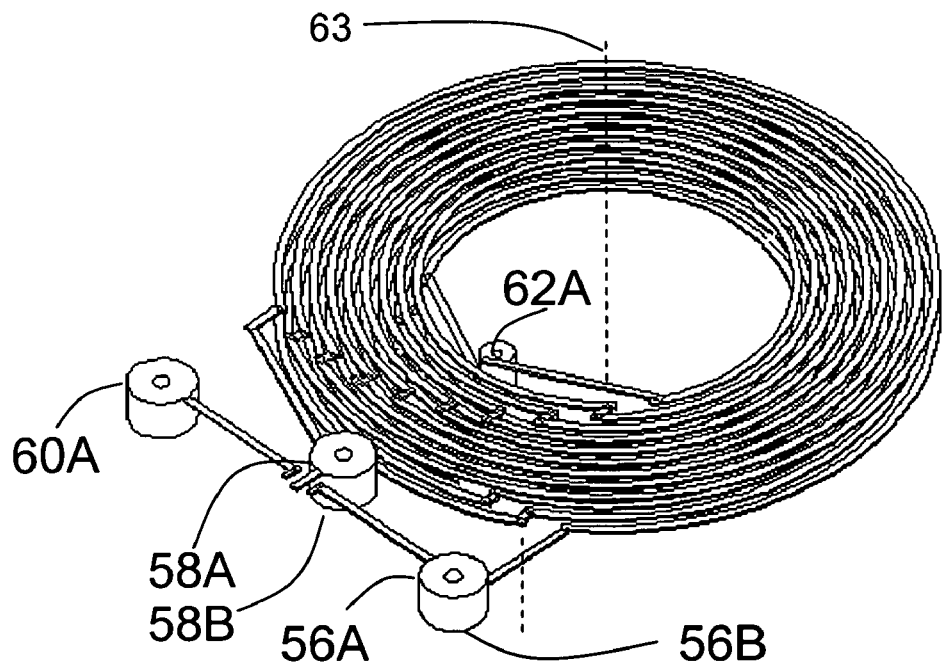
FIG. 11 is a perspective view of the sensor inductor or coil of FIG. 10 without the substrate but illustrating connections to the terminals.

A dual sensor inductor arrangement 50 is illustrated in FIGS. 10 and 11 wherein a single sensor substrate 52 includes separate sensor inductors 54A and 54B mounted on, formed on, or deposited on, opposite sides of the substrate, or formed within the substrate, and wound about the axis 63 in the same direction. The sensor inductors 54A and 54B are adapted to be interconnected via the terminals or connections 56A and 56B, 58A and 58B, 60A and 60B and 62A and 62B to function as unitary units. The sensor inductors or coils 54A and 54B can be substituted for the sensor inductor arrangements 10A and 10B in the embodiment of the sensor of FIGS. 4-9 and in such case the use of four sensor inductors, two per sensor substrate, increases the flux generation and reception, but as a dual sensor inductor assembly the sensor inductors electrically operates the same way as the embodiment with a single sensor inductor per sensor substrate.

Figure 12:
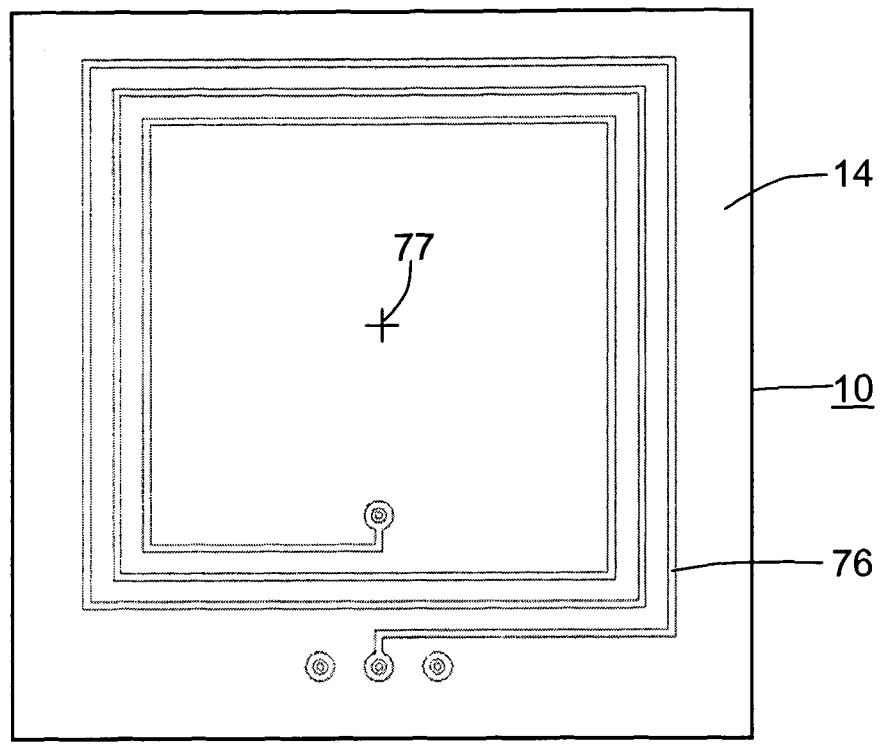
FIG. 12 is an embodiment of the sensor inductor of FIG. 1 illustrating a rectangular configuration.
Figure 13:
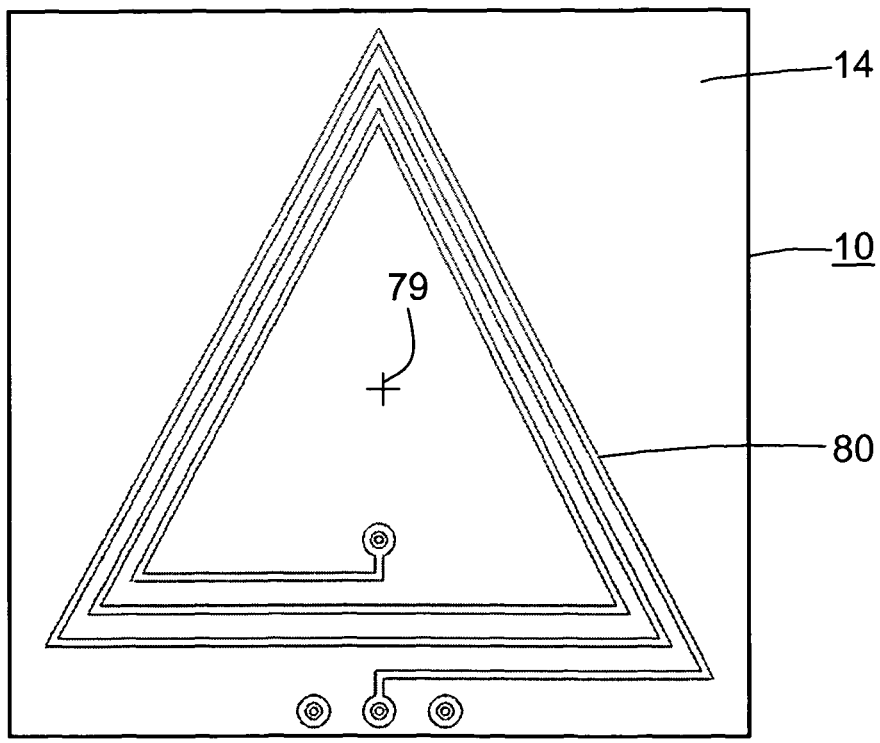
FIG. 13 is an embodiment of the sensor inductor of FIG. 1 illustrating a triangular configuration.
Figure 14:
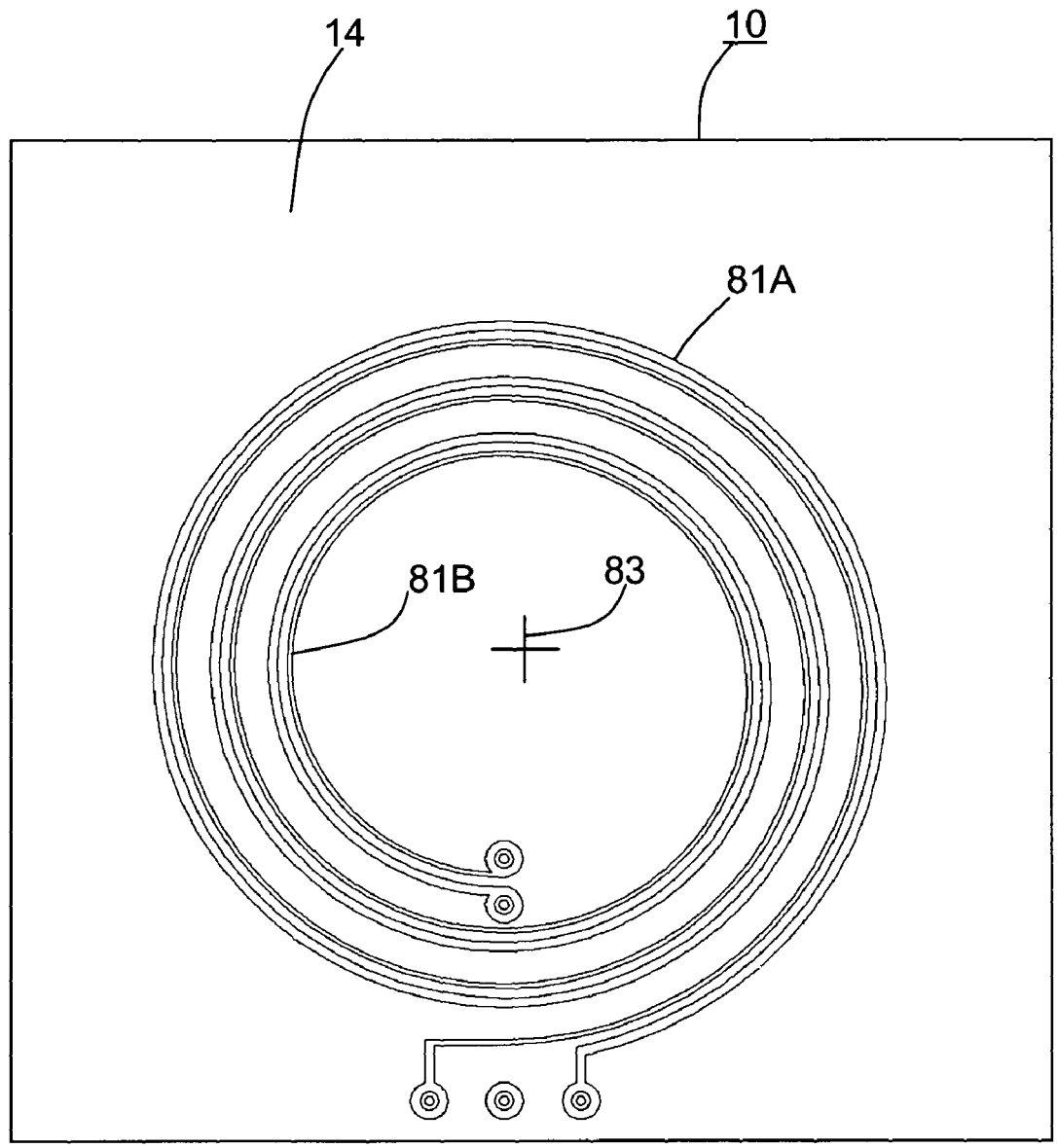
FIG. 14 is an embodiment of the sensor inductor of FIG. 1 with bifilar windings.
Figure 15:
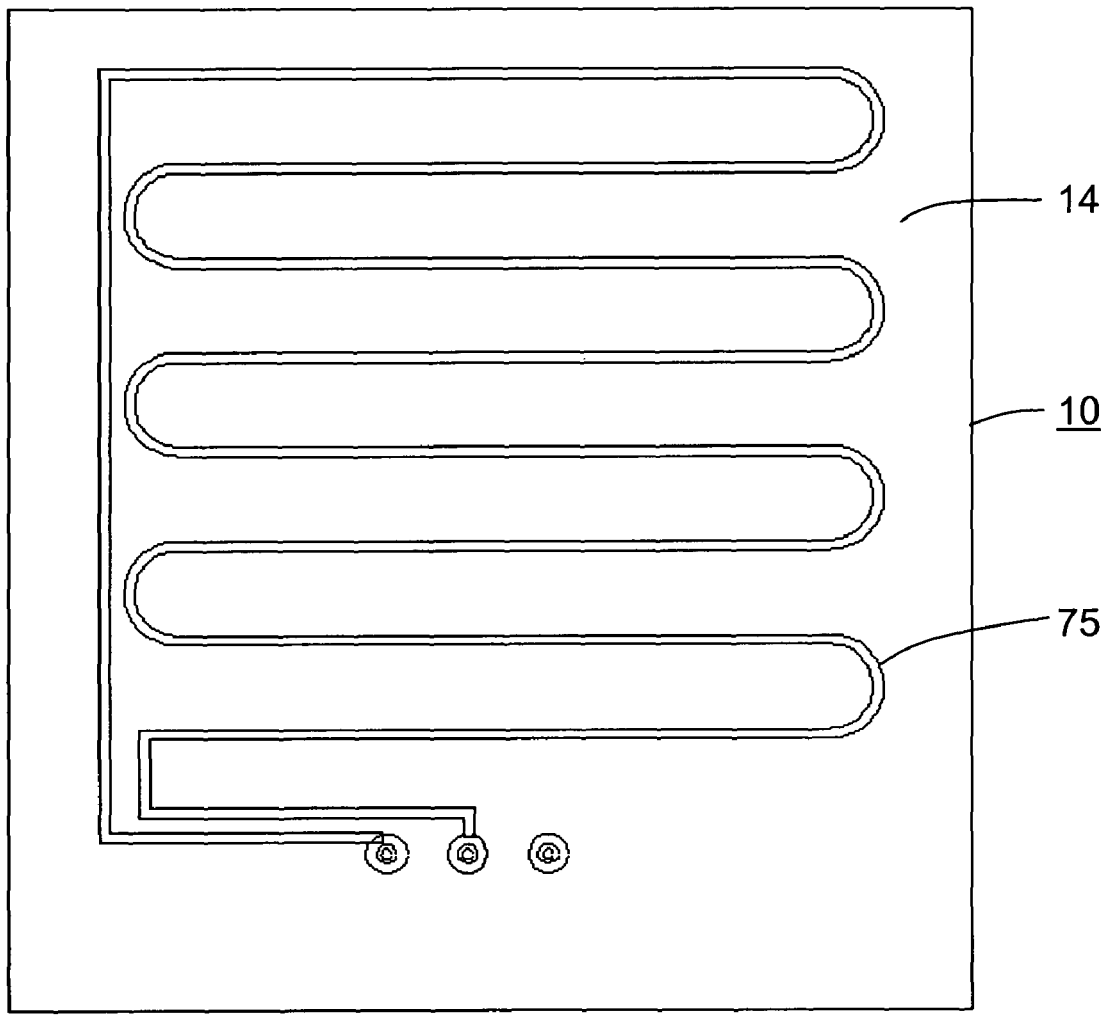
FIG. 15 is an embodiment of the sensor inductor of FIG. 1 illustrating the inductor in a serpentine configuration.

Although the sensor inductor 10 described above included conductors 12 formed or deposited in a circular form, it should be understood the conductors 12 can be tailored to have a variety of shapes, depending upon the linearity, non-linearity, or special response desired, such as for example as a rectangular shaped conductor 76 of FIG. 12 formed about the axis 77, or a triangle shaped conductor 80 of FIG. 13 formed about the axis 79, or the bifilar windings 81A and 81B of FIG. 14 formed about the axis 83, or the serpentine shaped conductor 75 of FIG. 15. The conductor could also be in a variety of other shapes and forms, such as having regular patterns as a star, or irregular patterns such as a leaf, as the design requirements for the sensors dictate. Further the size, width, or thickness of the conductor 12 need not be uniform and can vary.

Figure 16A:
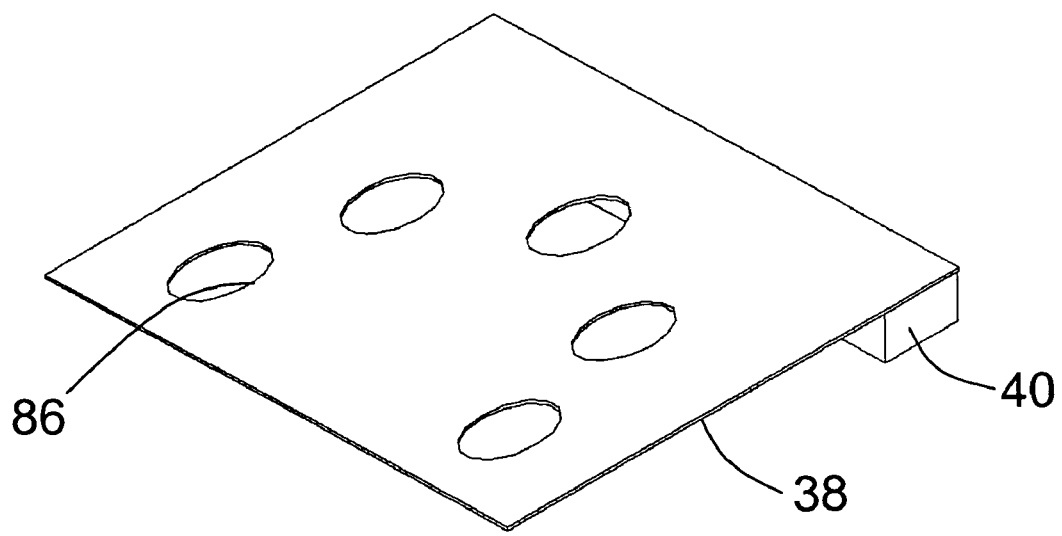
FIGS. 16a and 16b are illustrations of embodiments of an armature configuration.
Figure 16B:
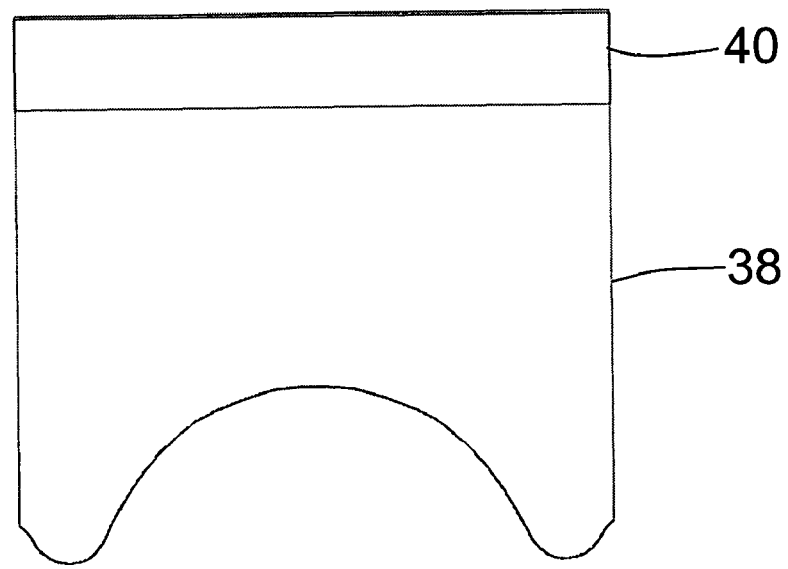
Figure 17:
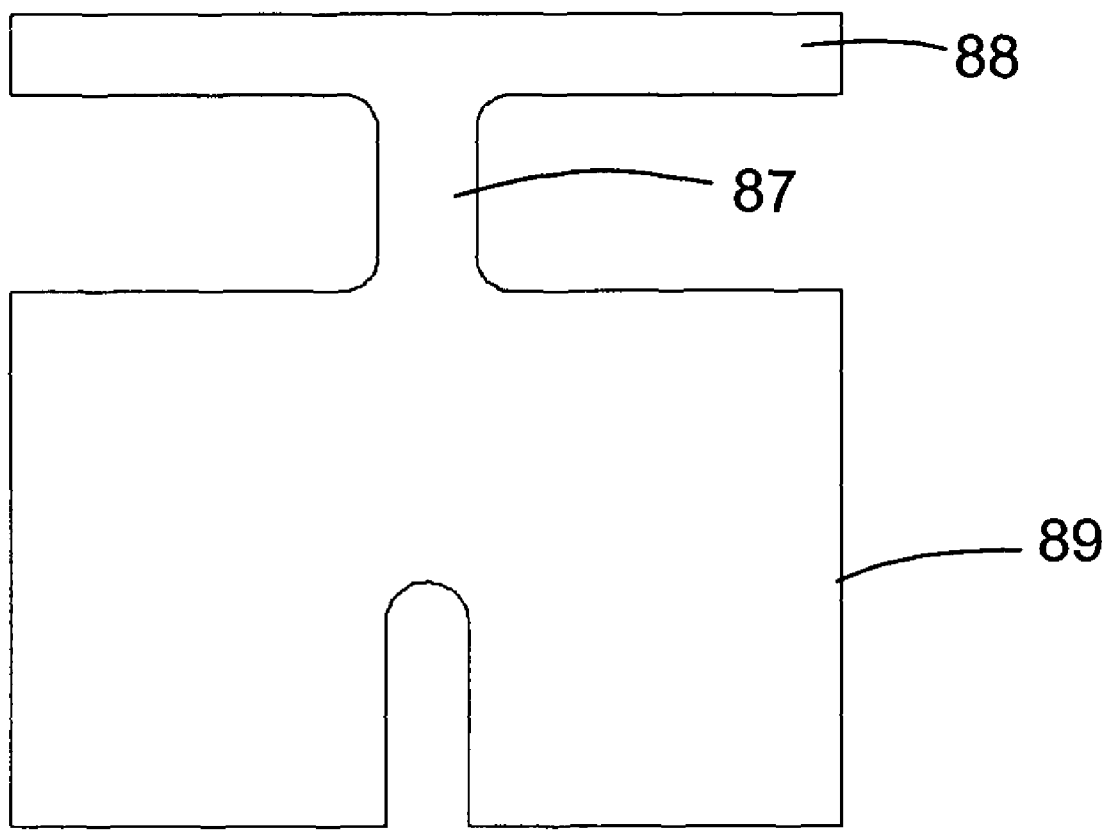
FIG. 17 is another embodiment of an armature configuration with a flexible portion
Figure 18:
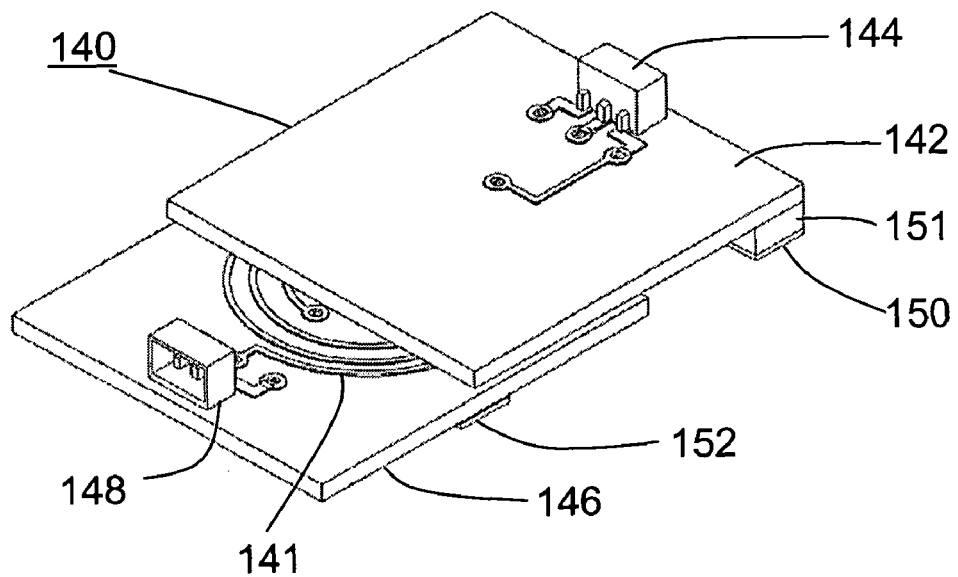
FIG. 18 is a perspective view of another embodiment of the sensor of the invention including a movable sensor inductor as the armature.
Figure 19:
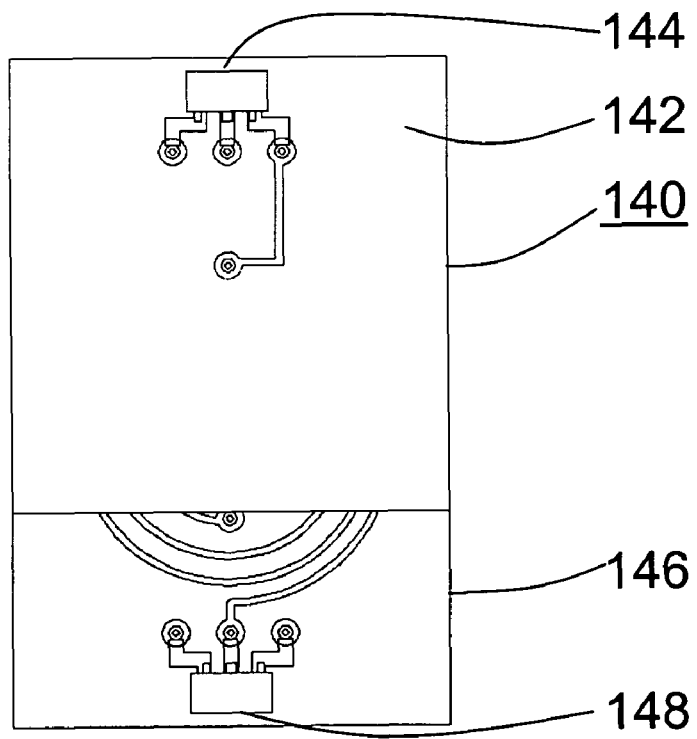
FIG. 19 is a top view of the sensor of FIG. 18.
Figure 20:
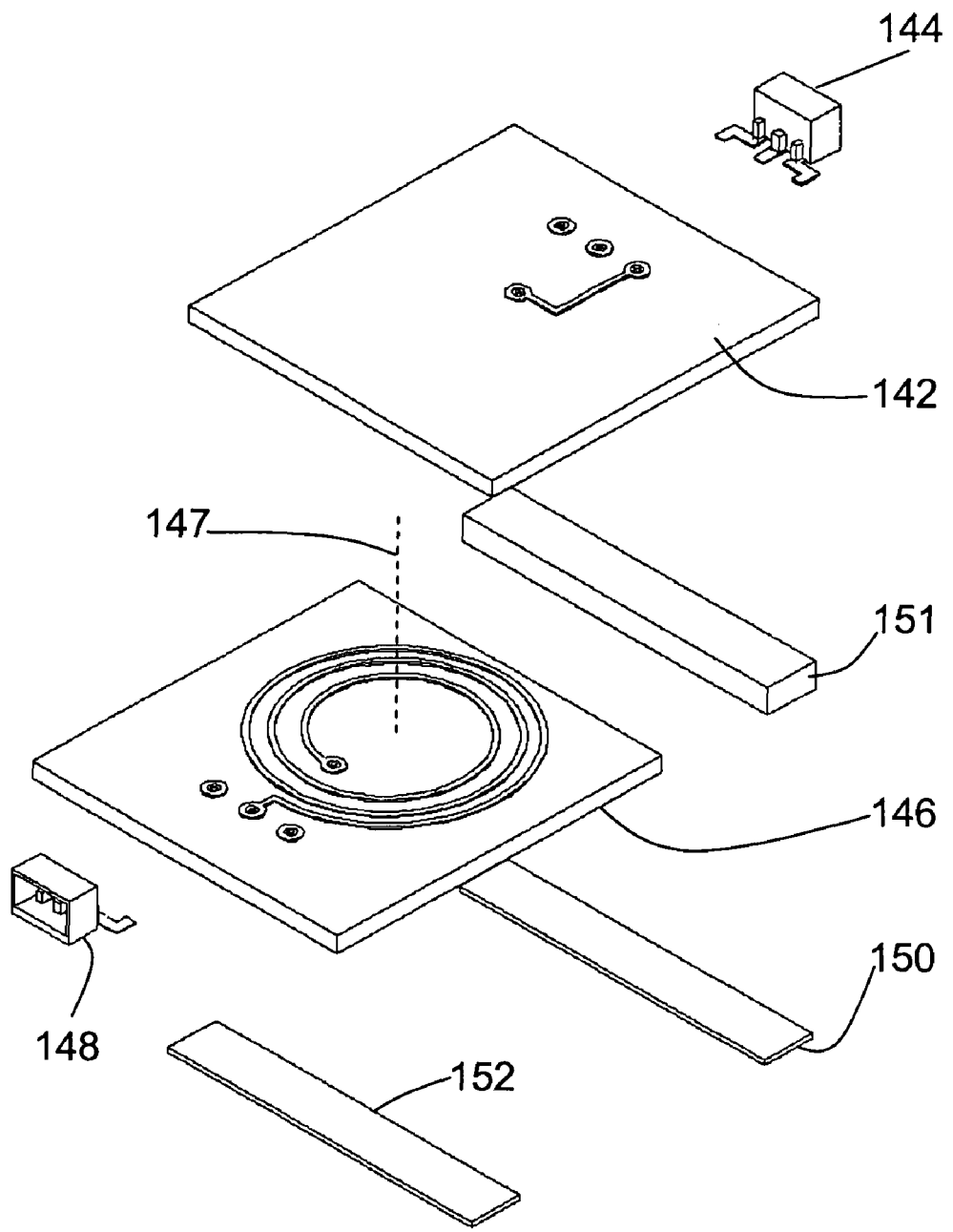
FIG. 20 is an exploded view of the sensor of FIG. 18.
Figure 21:
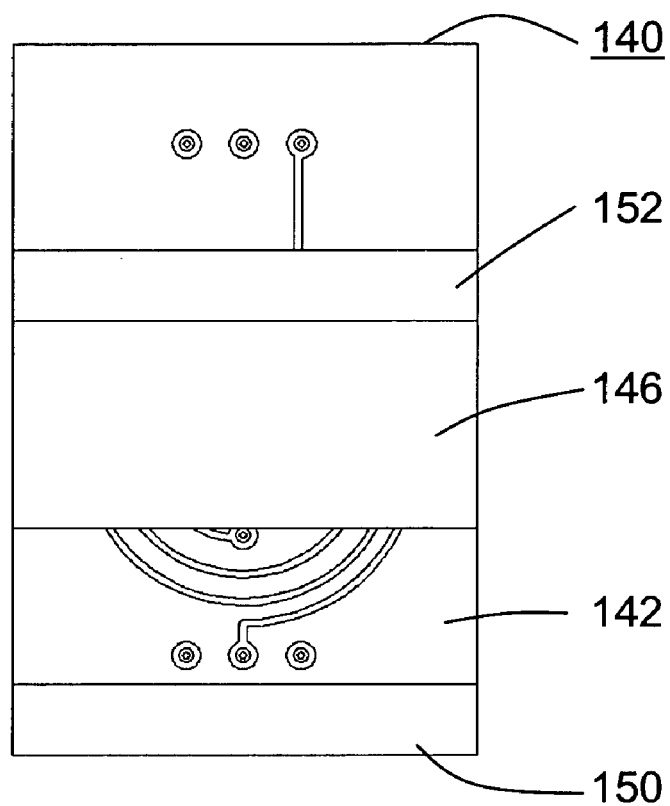
FIG. 21 is a bottom view of the sensor of FIG. 18.
Figure 22:
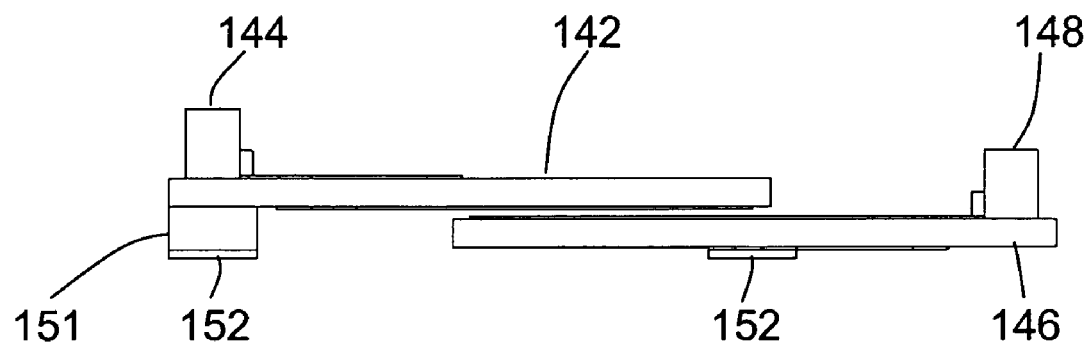
FIG. 22 is a side view of the sensor of FIG. 18.
Figure 23:
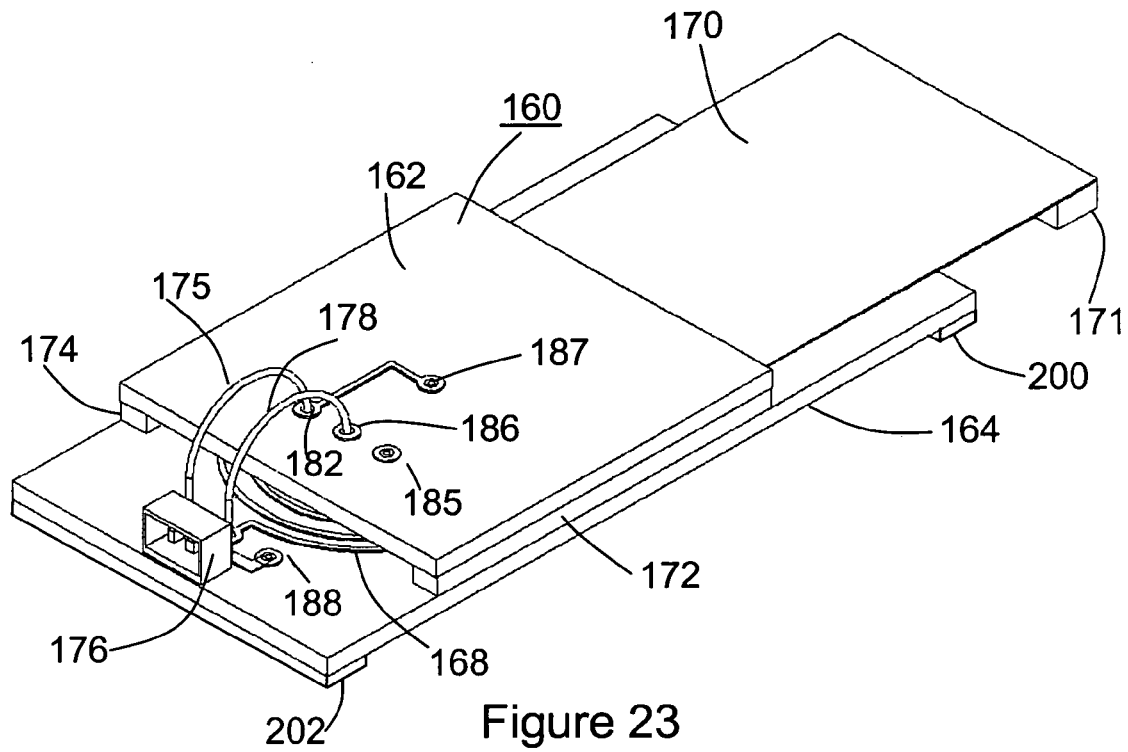
FIG. 23 is a perspective view of another embodiment of the sensor of the invention wherein the armature includes two sensor inductors.
Figure 24:
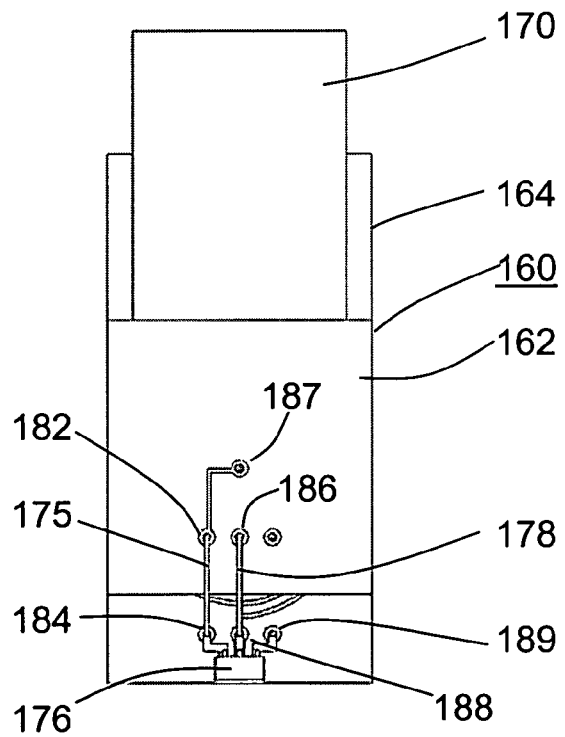
FIG. 24 is a top view of FIG. 23.
Figure 25:
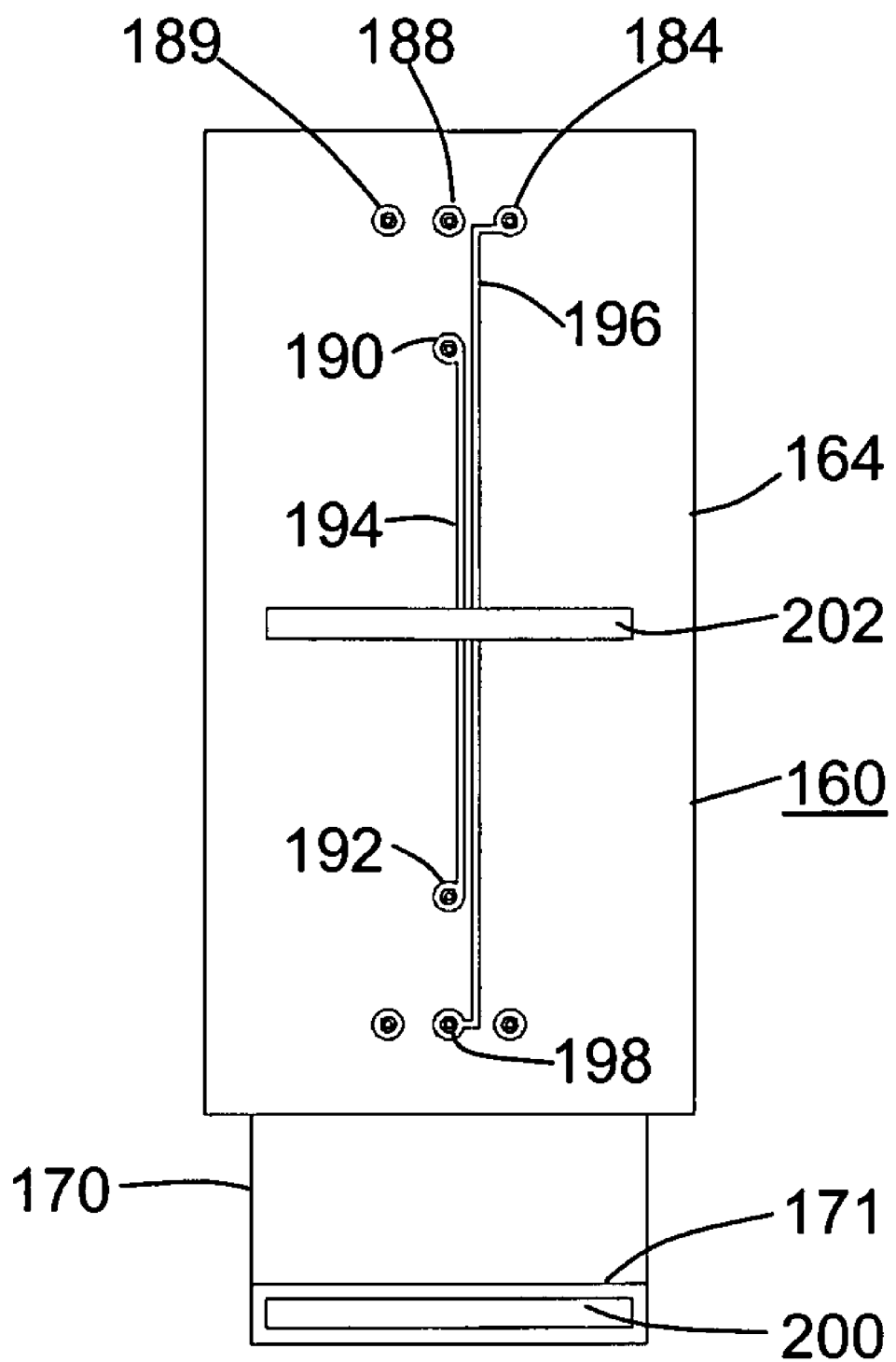
FIG. 25 is a bottom view of FIG. 23.

In addition, the size and thickness of the armature 38 can be tailored for the linearity, non-linearity, or special response desired, such for example, but not limited thereto, to be formed with perforations 86 of FIG. 16a, the contoured shape of FIG. 16b, or the armature of FIG. 17 having a substrate attachment portion 88, a flexible arm 87 as an attaching the attachment portion 88 to the main portion 89 of the armature. The flexible arm 87 reduces the amount of twisting movement of the surface under test that is transmitted to the main portion 89 of the sensor armature reducing its impact on the magnetic field between the inductors.

While the resulting Q of the inductors of the sensor of the invention is quite low compared to the Q of the convention sensor inductors, the low Q of the inductors is sufficient for use with the motion detecting techniques described herein.

With regard to the embodiment of the sensor of FIGS. 18-22, a bottom sensor inductor 141 and a top sensor inductor on sensor substrate 142 (not shown) are movable with respect to each other. Separate connectors 144 and 148 are provided for the sensor inductors. Signal inputs can be applied to the connector 144 and output signals received from connector 148, or visa versa. Pads 150 and 152 are provided for mounting the substrates on a surface to be monitored. A mount 151 and adhesive pad 150 is provided for mounting the substrate 142 to the surface under test. Adhesive pad 152 is provided for mounting substrate 146 to the surface under test. Input signals can be applied to connector 144 or 148 and output signals received from the other connector. The magnetic flux lines flow between the inductors 142 and 146 generally normal to the planes of the inductors in a manner as illustrated in FIG. 9. When the sensor inductors are spaced over each other the signal output goes to zero. When the sensor inductors move away from the zero position the output signal changes until another zero is reached when the other sensor inductor is fully retracted. Hence the output signal will have zero positional indications with maximum points as the relative position changes. This arrangement has the advantage of not being temperature sensitive.

Figure 26:
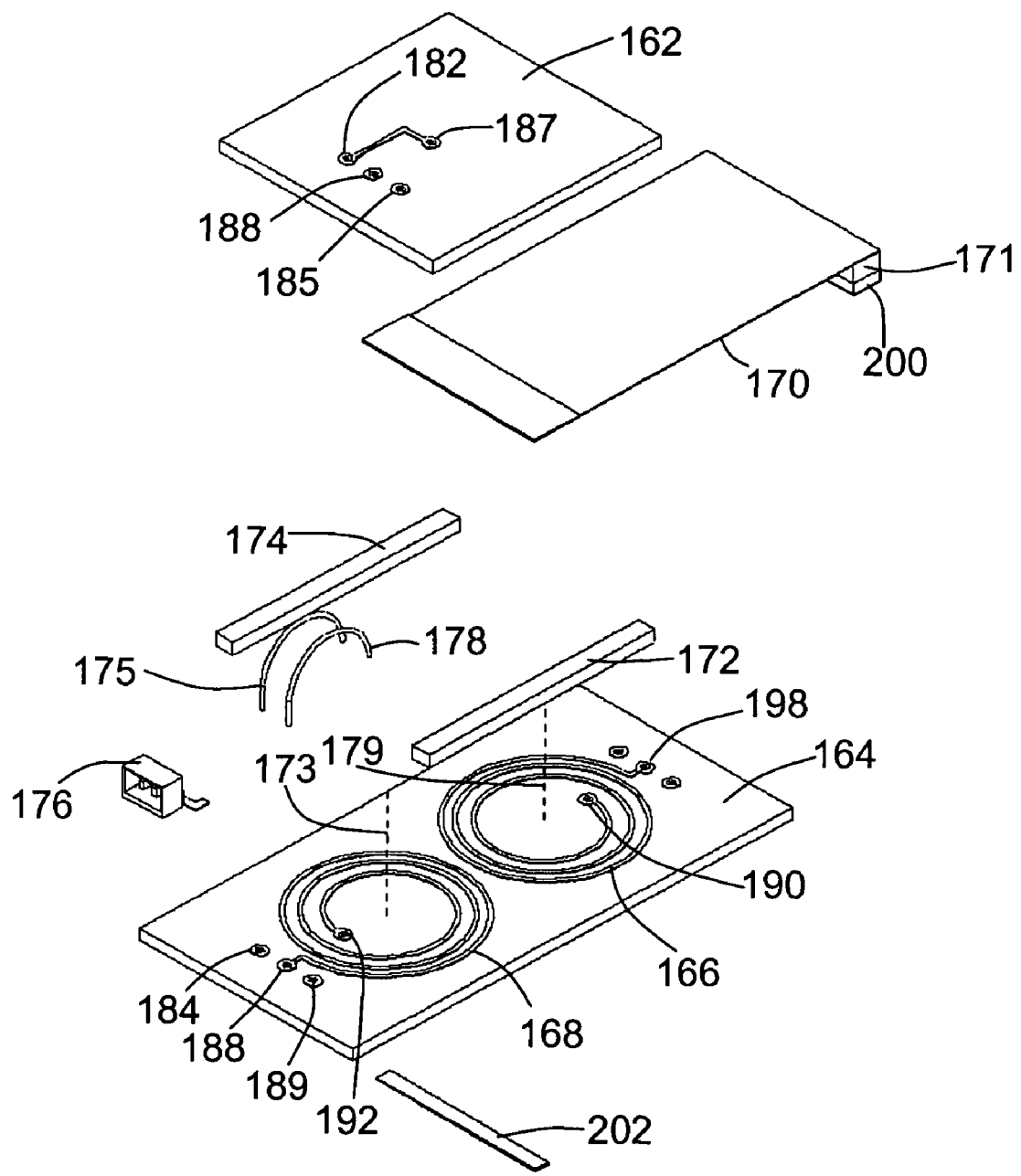
FIG. 26 is an exploded view of the sensor of FIG. 23.
Figure 27:
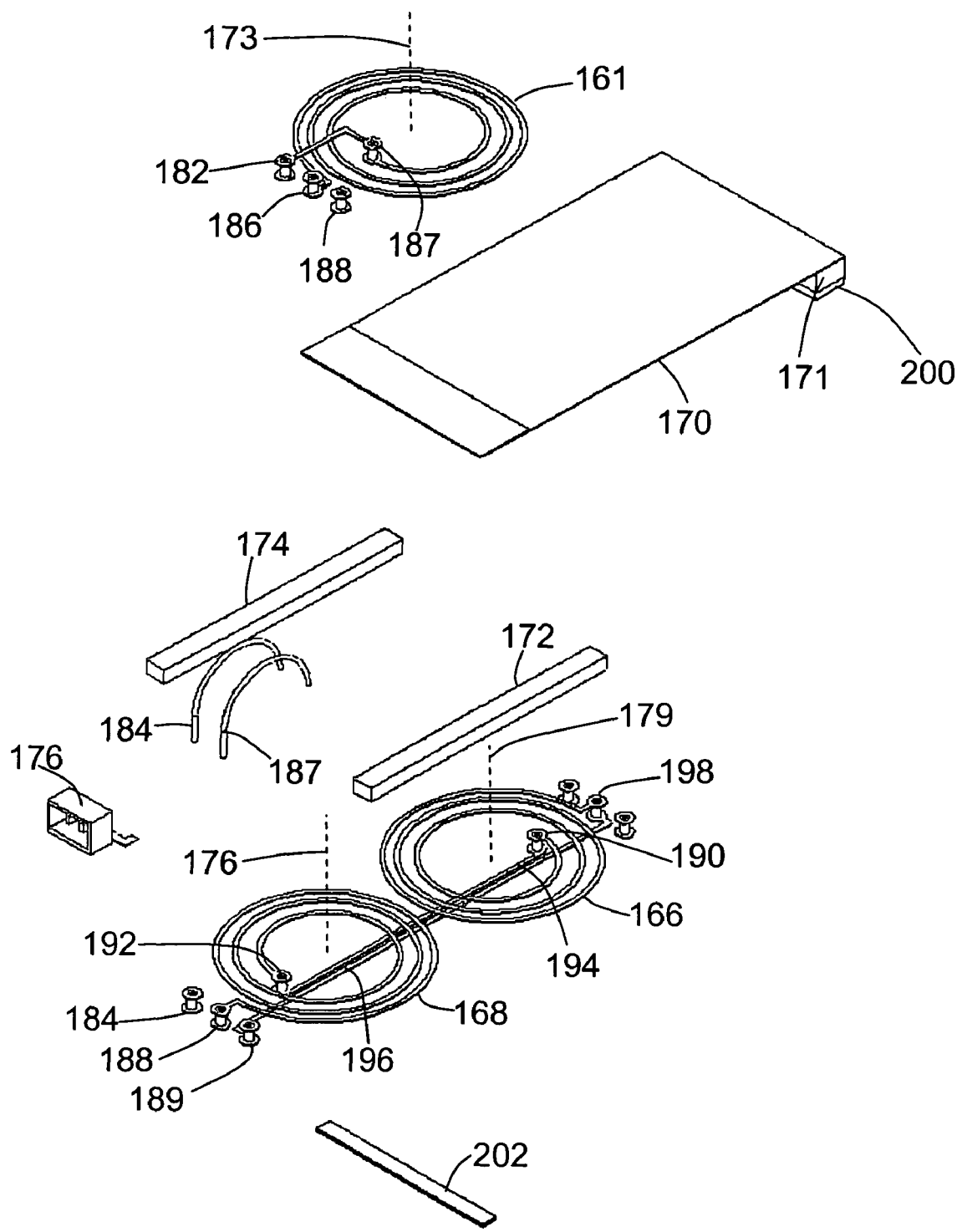
FIG. 27 is an exploded view of the sensor of FIG. 23 without the substrates.
Figure 28:
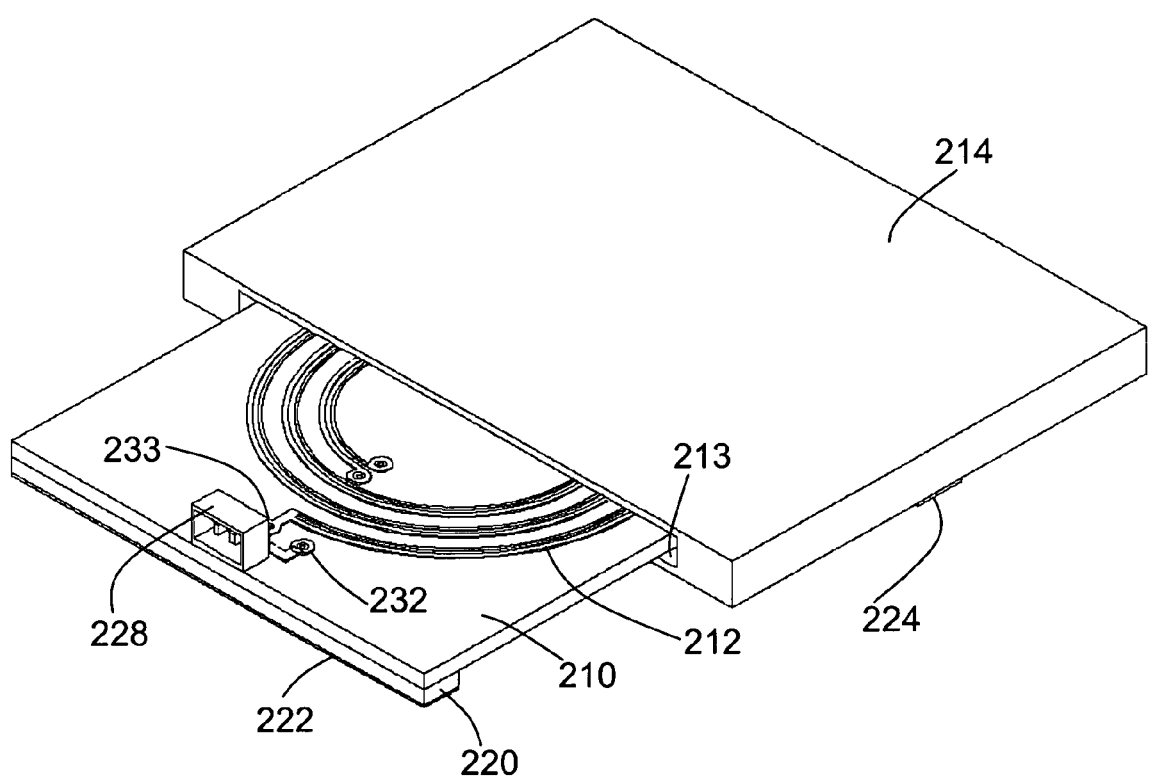
FIG. 28 is perspective view of another embodiment of the invention wherein the armature includes bifilar sensor inductors.
Figure 29:
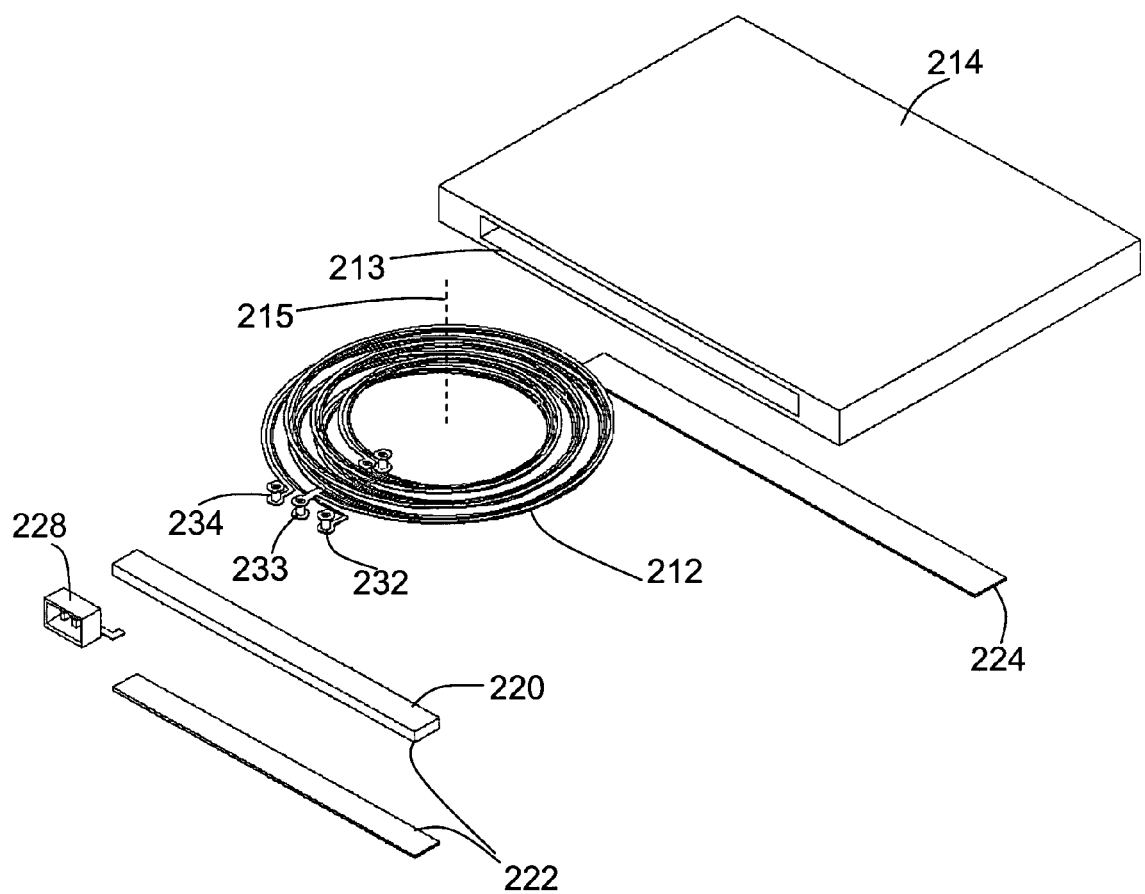
FIG. 29 is an exploded view of the sensor of FIG. 28 without the armature substrate.
Figure 30:
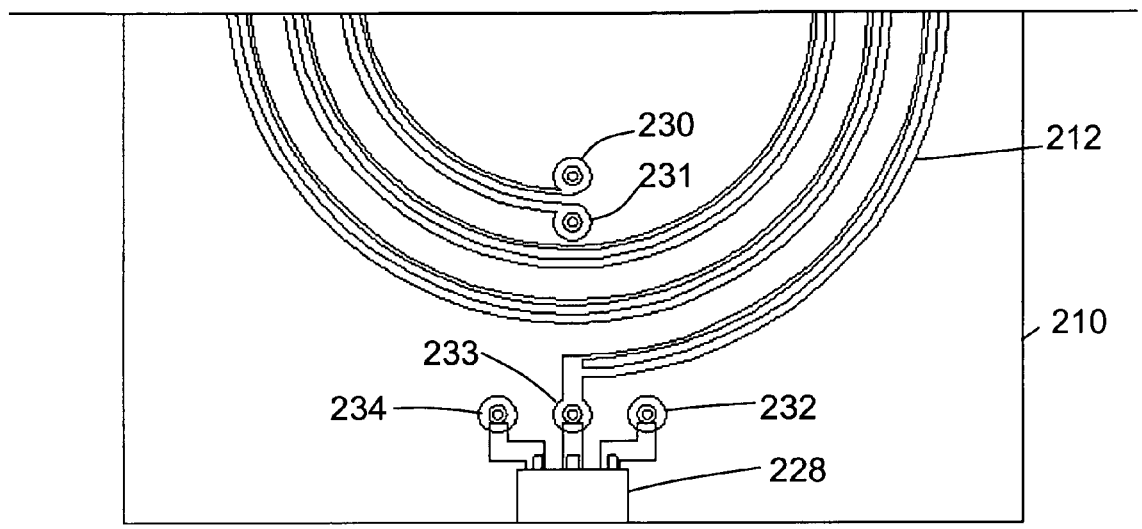
FIG. 30 is a top view of part of the bifilar sensor inductor of FIG. 28.
Figure 31:
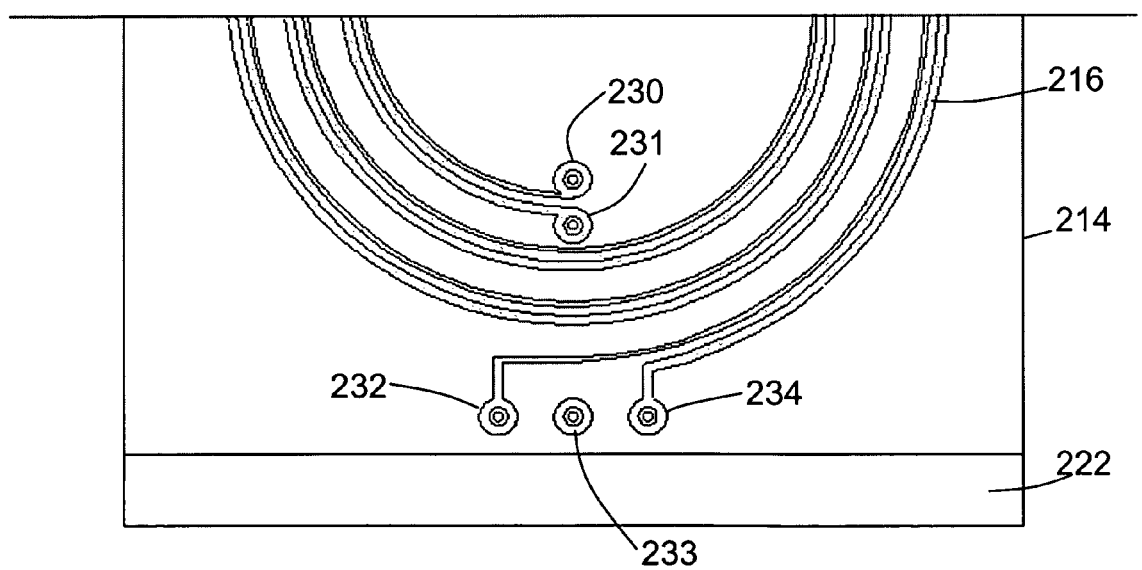
FIG. 31 is a bottom view of part of the bifilar sensor inductor of FIG. 28.
Figure 45:
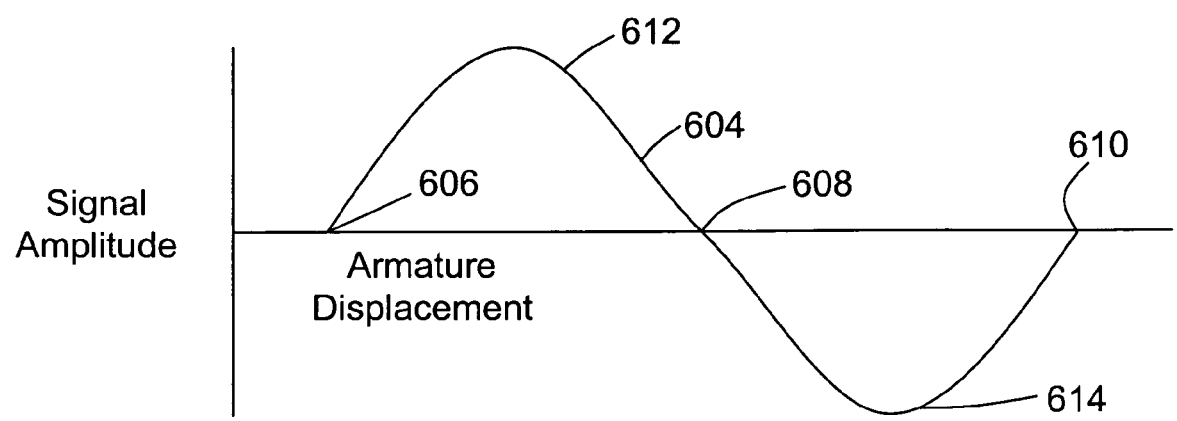
FIG. 45 illustrates the operation of the sensor of FIG. 23 to provide relative and positional displacements.

In the sensor 160 embodiment of the invention of FIGS. 23-27, the top sensor substrate 162 includes a generally planar sensor inductor or coil 161. A bottom sensor substrate 164 includes two generally planar spaced apart sensor inductors or coils 166 and 168 in serial juxtaposition and wound about separate axis 173 and 179 (FIG. 26). Two spacers 172 and 174 separate the top and bottom sensor substrates 162 and 164. A shielding armature 170 with an attachment mount 171 is positioned to move within the substrate spacing and relative to the sensor inductors 161, and 166 and 168. A connector 176 is connected to the terminals 184, 188 and 189 of the sensor substrate 164. The wire 178 connects the terminals 186 and 188. A wire 175 connects terminals 182 and 184. As illustrated in the bottom view of the sensor (FIG. 25), terminals 184 and 198 on the substrate 164 is connected by connection 196, and the terminals 190 and 192 are connected by the connection 194. An adhesive pad 200 is located on armature mount 171 and adhesive pad 202 is provided for the sensor substrate 164 for mounting purposes. The sensor arrangement of FIGS. 23-27 with an excitation signal applied to the coil 161, the coils 166 and 168 provide an indication of the location of the armature 170 relative to the sensor inductors 161, 166, and 168 as well as a positional indication as the armature follows the surface being monitored, as illustrated in FIG. 45 by the curve 604 having three zero points 606, 608, and 610, and change in polarity.

The sensor embodiment of FIGS. 28-31 includes a magnetic shield 214 with a slot opening 213 into which a sensor inductors and substrates are adapted to move in and out of the magnetic shield. The sensor inductors 212 are bifilar of the type illustrated in FIG. 14 formed on both sides of the sensor substrate 210 wound about the axis 215. The inductors are interconnected via the terminals 230-234. One inductor on each side of the sensor substrate 210 serves as the excitation inductor, and the other the output inductor. A connector is provided for the application of input signals and the receipt of output signals. The sensor inductor 210 has a mount 220 and an adhesive pad 222 adapted to be connected to a surface to be monitored. The magnetic shield 214 is adapted to be mounted on the surface via adhesive pad 224. As the sensor inductors are inserted deeper into the magnetic shield the magnetic flux field is enhanced and the amplitude of the output signals is increased and visa versa.

Figure 32:
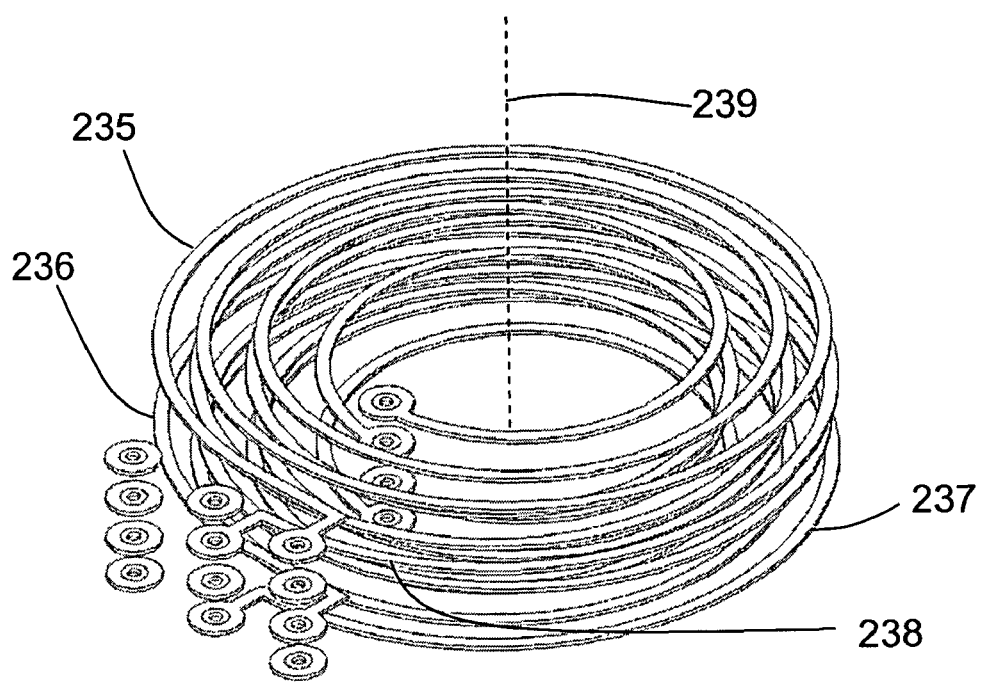
FIG. 32 is a perspective view of a stacked multi sensor inductor embodiment without substrates.
Figure 33:
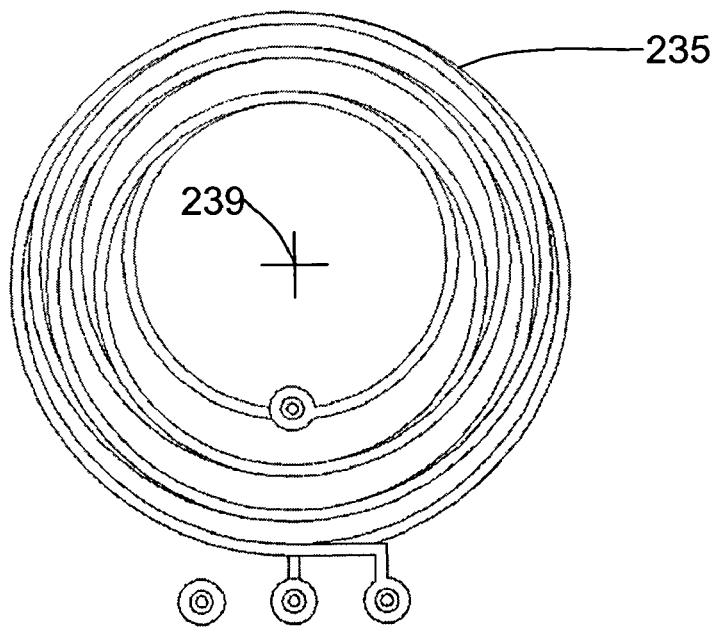
FIG. 33 is a top view of the stacked multi sensor inductor embodiment of FIG. 32.

In FIGS. 32 and 33 sensor inductors on substrates (not shown) can be assembled as multiple stacked layers of sensor inductors 235-238 wound about the axis 239 and armatures (not shown) may be inserted between pairs of sensor inductors to tailor the sensor for monitoring multiple operations.

Figure 34:
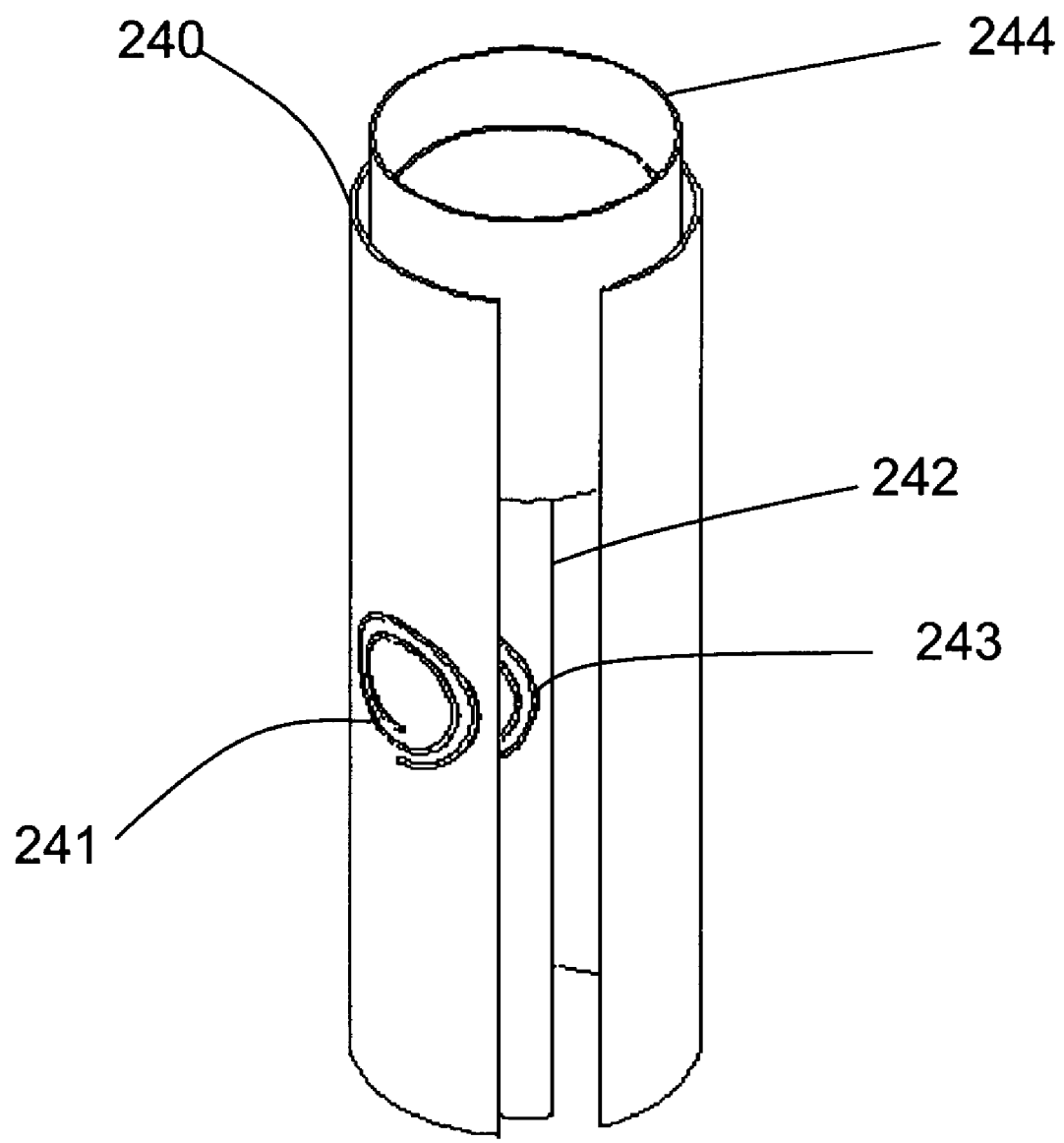
FIG. 34 is a perspective view of the sensor applied to cylinders.

In FIG. 34 the sensor inductors 241 and 243 are illustrated mounted on cylindrical sensor substrates 240 and 242 and curved to fit the couture of the cylinders. A cylindrical armature 244 is adapted to be positioned between the substrates 240 and 242 and the sensor inductors 241 and 243 to provide an indication of the relative positions of the substrates and the armature.

Figure 35:
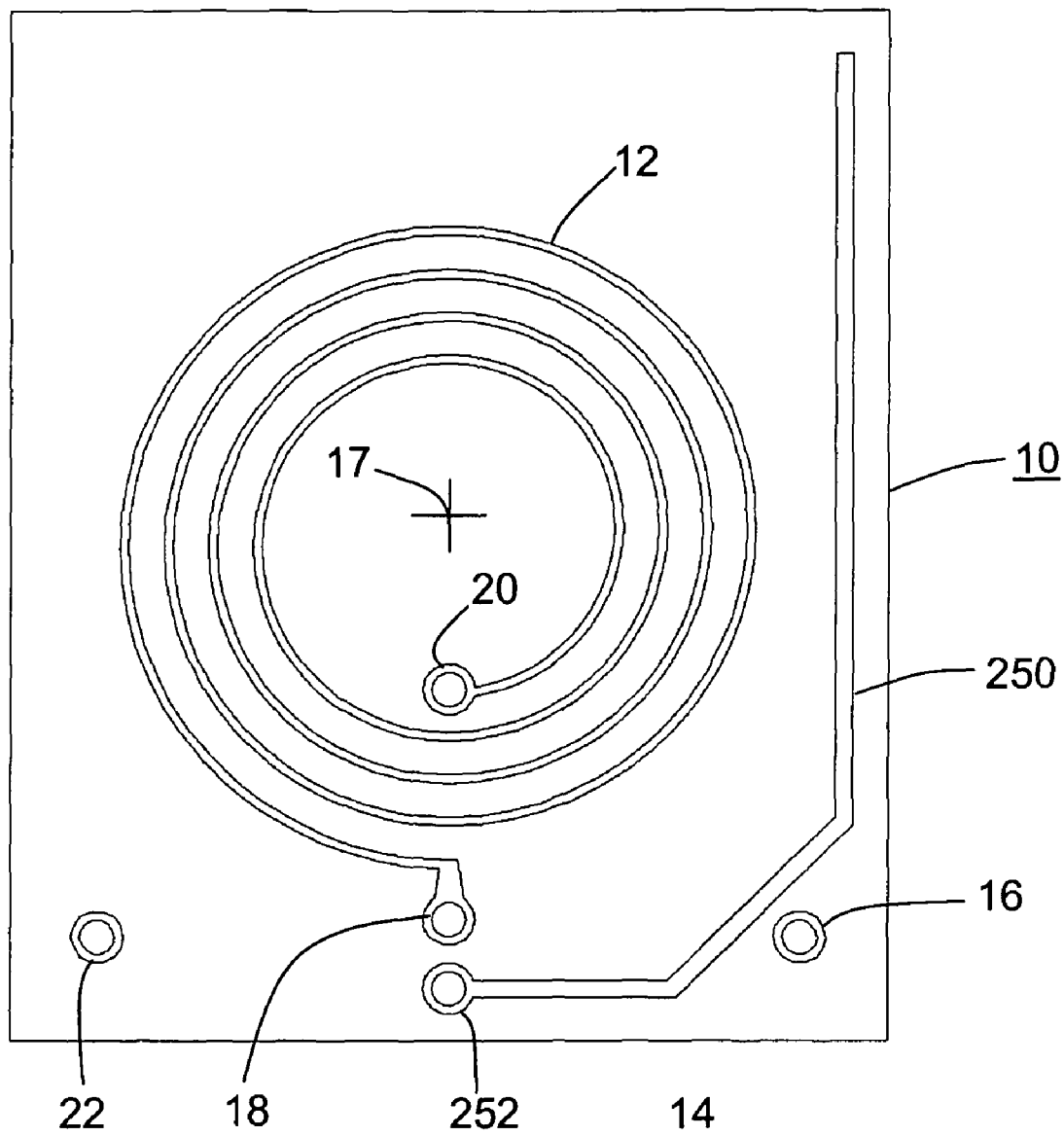
FIG. 35 is an embodiment of the sensor inductor or coil of FIG. 1 with an antenna formed thereon.
Figure 40:
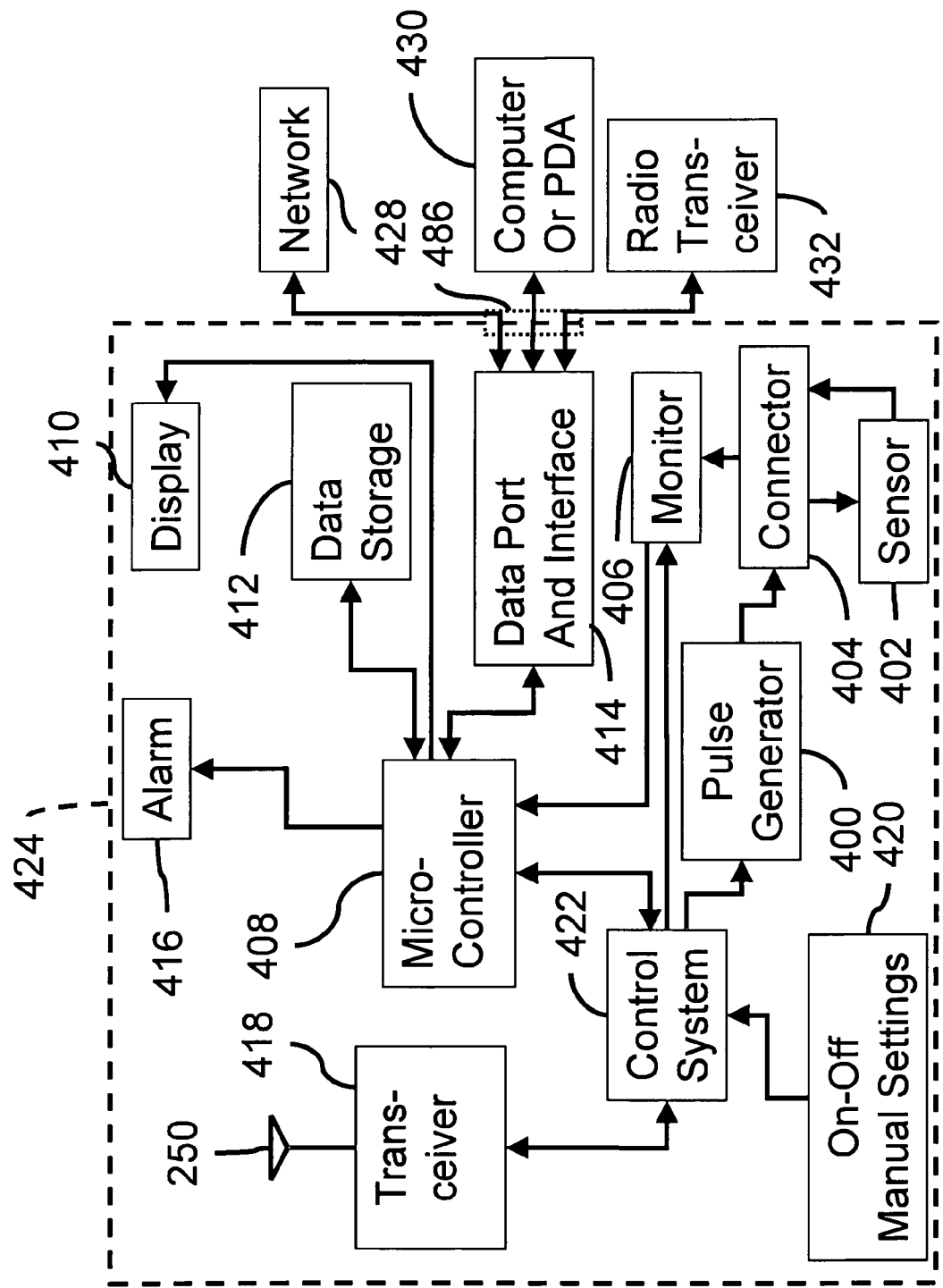
FIG. 40 is a basic block diagram of an embodiment of a monitoring system for use with the sensor inductors.

The sensor inductor of FIG. 1 has been modified in FIG. 35 to include an antenna structure 250 formed on the sensor substrate 14 and is adapted to be connected via terminal 252 to the monitoring system transceiver 418 of FIG. 40.

Figure 36:
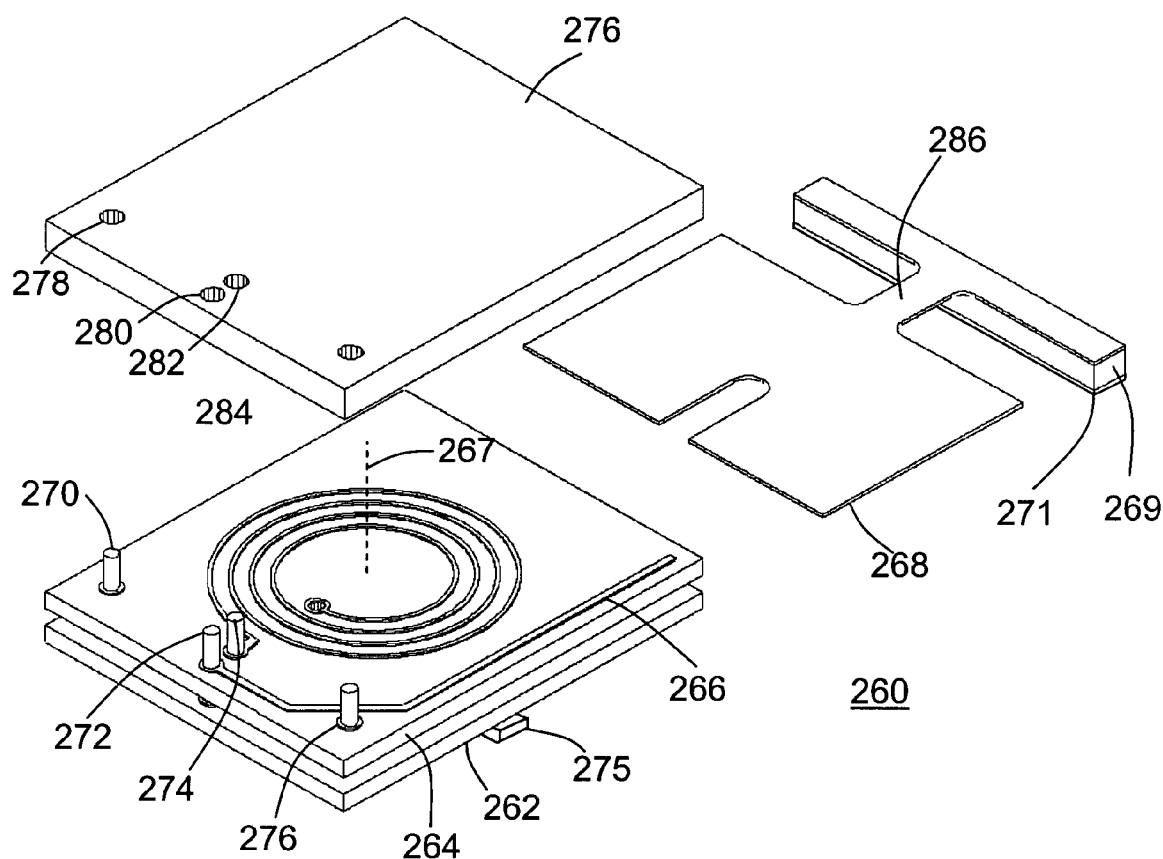
FIG. 36 is an exploded view of a sensor system including the armature of FIG. 17 and a detachable electronics unit.
Figure 37:
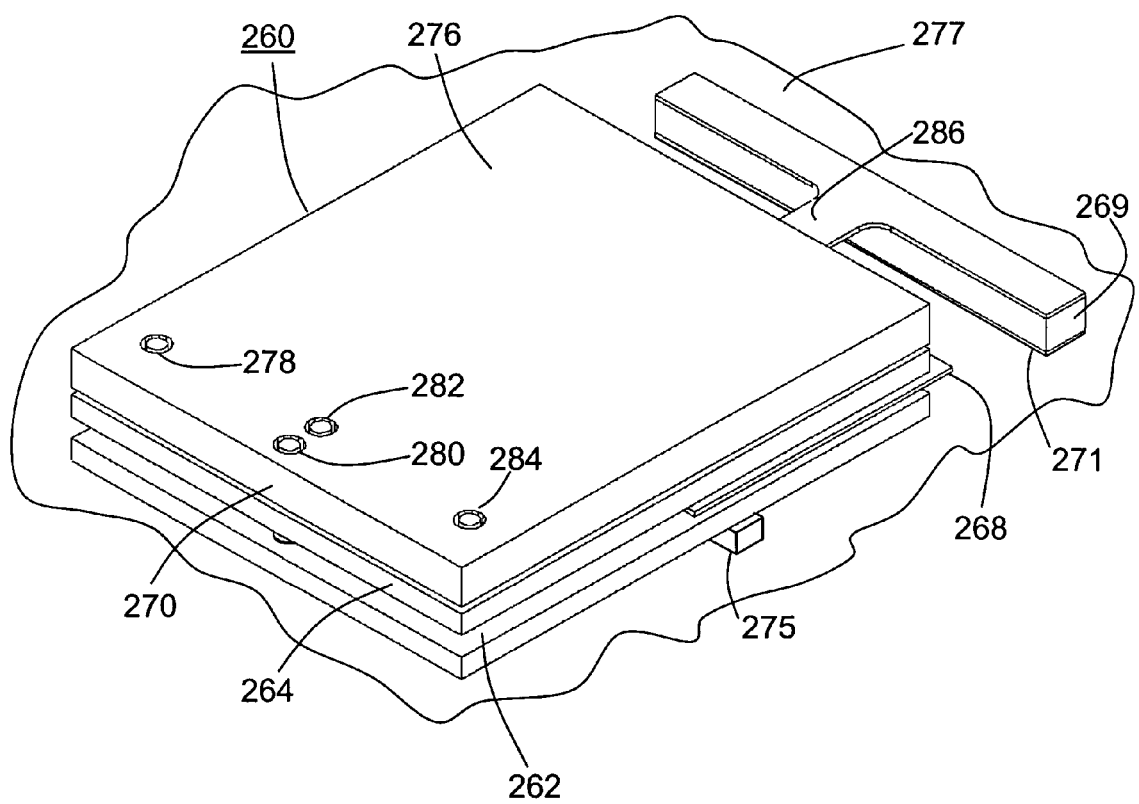
FIG. 37 is a perspective view of the sensor system of FIG. 36.

FIGS. 36 and 37 illustrate the combined sensor and monitoring system 260. The sensor includes two double-sided sensor inductors 262 and 264 of the type shown in FIGS. 10 and 11 wound on the sensor substrate about the axis 267. At least one inductor includes an antenna 266. An armature 268 of the type illustrated in FIG. 17 is adapted to be positioned between the substrates of sensor inductors 262 and 264. The armature 268 includes a mount 269 connected via a flexible neck 286 to the armature portion 268. An adhesive pad 271 is included on the mount 269 for attachment of the sensor to a surface 277 to be monitored. The sensor inductors include the pad 275 for attachment to the surface. The monitoring system 276 is snapped into connection with the sensor inductors via sensor inductor terminals 270, 272, 274, and 276 and monitoring system terminals 278, 280, 282, and 284. It should be understood that the terminal connection between the monitoring system and the sensor inductors is exemplary and other type of quick connect and disconnect could be used When the sensor 260 is attached to a surface 277 as illustrated in FIG. 37, deformations or stretch of the surface 277 between the armature adhesive pad 271 and the sensor inductor substrate adhesive pad 275 (surface under test) is reflected as movement of the armature 268 in and out of the sensor. Input signals are adapted to be applied to one of the sensor inductors (excitation sensor inductor) and the other sensor functions as the output sensor inductor. If the surface under test is compressed the armature 268 moves further into the sensor and the amount of flux transmission of the input signal between the sensor inductors 262 and 264 is increased. If the surface under test expands, the armature withdraws from the sensor and the amount of flux transmission of the input signal between the sensor inductors is decreased. These changes of flux transmission are reflected as signals from the out sensor inductor and are received by the monitoring system 276, and are converted to indications of the movement of the surface under test. The flexibility neck 286 in the armature reduces the amount of twisting motion of the surface that is transmitted to the movement of the armature 268 within the sensor. The arrangement is such that the sensor inductors 262 and 264 can be removed from the monitoring system 276 via a snap connector and the monitoring system reused while the sensor inductors can be discarded or cleaned for reuse.

Figure 38:
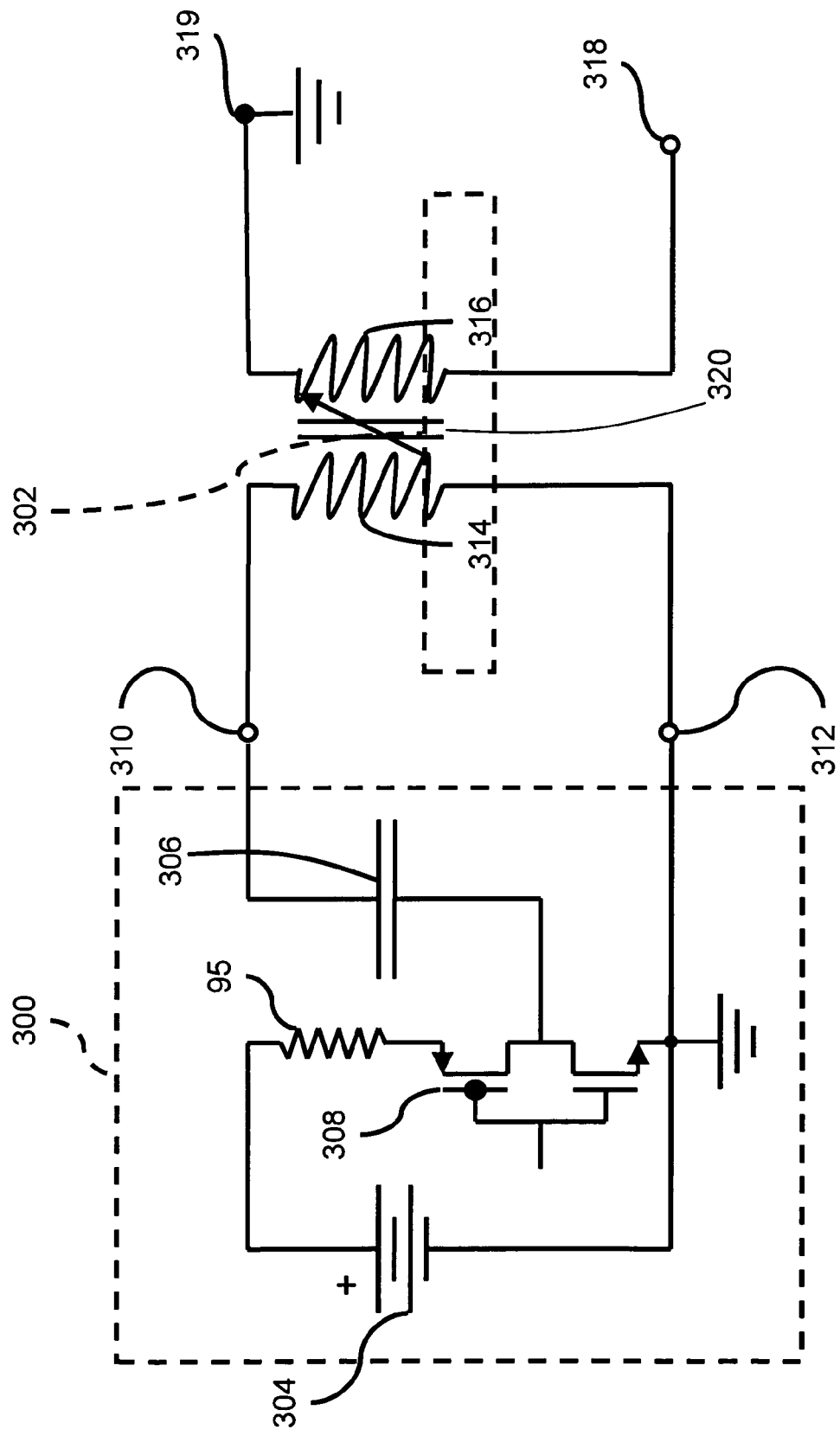
FIG. 38 is an electrical schematic drawing of the sensor inductors and a circuit for applying pulses to the sensor.

FIG. 38 is a schematic diagram of an embodiment of a pulse type generator 300 for use with the sensor inductor 302 of the invention illustrated in the schematic form. Circuit 300 is illustrated as an electrical equivalent circuit, including a power source illustrated as a battery 304, a capacitor 306, and a switching semiconductor 308 such as a power CMOS inverter (although other semiconductor circuit designs could be used). Capacitor 306 can have a value in the order of 4.7 microfarads. The circuit 300 is connected through the connector terminals 310 and 312 to apply pulses to a sensor inductor 314 designated as the excitation inductor. The response from sensor inductor 316 is applied to the connector terminals 318 and 319. The armature 320 extends between the sensor inductors 314 and 316.

When semiconductor 308 is switched into its charging condition, the capacitor 306 is charged to the voltage value of the battery 304 (3.3 volts) through the winding 314. The capacitor's charge time constant is selected for about one millisecond. When the semiconductor 308 is switched to the discharge condition, the charge across the capacitor 306 is discharged via the inductor 314 and the sensor inductor 316 outputs the response as a function of the relative positioning between the sensor inductors 314 and 316 and the armature 320 as illustrated by the decaying signal 330 in FIG. 39. The discharge time through the sensor inductors is in the order of about one microsecond, depending upon the various reactive impedances and resistances exhibited by the sensor inductors. When the capacitor 306 is subsequently recharged, the current through the sensor inductor 314 is reversed eliminating some magnetic hysteresis that may have been created in the armature, through slow charging of the capacitor 306. It should be understood that other switching arrangements can be used in which the capacitor 306 is not recharged through the sensor inductor 314. The power consumption of the sensor per capacitor 306 charge and discharge is very low, greatly reducing the power supply demands for portability.

The amplitude of the voltage across the terminal 318 and 319 with the armature 320 inserted in place is the amplitude of voltage generated across the sensor inductor 316. When the sensor inductor 316 is connected to a high impedance circuit, any intrinsic capacitance and resistance have negligible effect.

In operation, when a signal voltage is applied across the terminals 310 and 312, current flows through the sensor inductor 314, flux lines are created that to through sensor inductor 316 and a voltage is induced in the sensor inductor 316 that appears across terminals 318 and 319. With the same number of conductor turns in both the sensor inductors 314 and 316, the magnitude of the voltage across terminal 312 and 318 is less than that as applied across terminals 310 and 312 due to losses within the circuit. When the armature 320 is inserted between the sensor inductors 314 and 316, it functions as a shield to block some of the flux lines transmitted between the sensor inductors wherein the magnitude of the voltage generated across the terminals 312 and 314, in response to input signals is reduced. The further the armature 320 is inserted between the sensor inductor, the higher magnitude of voltage is generated across the terminals 318 and 319.

Figure 39:
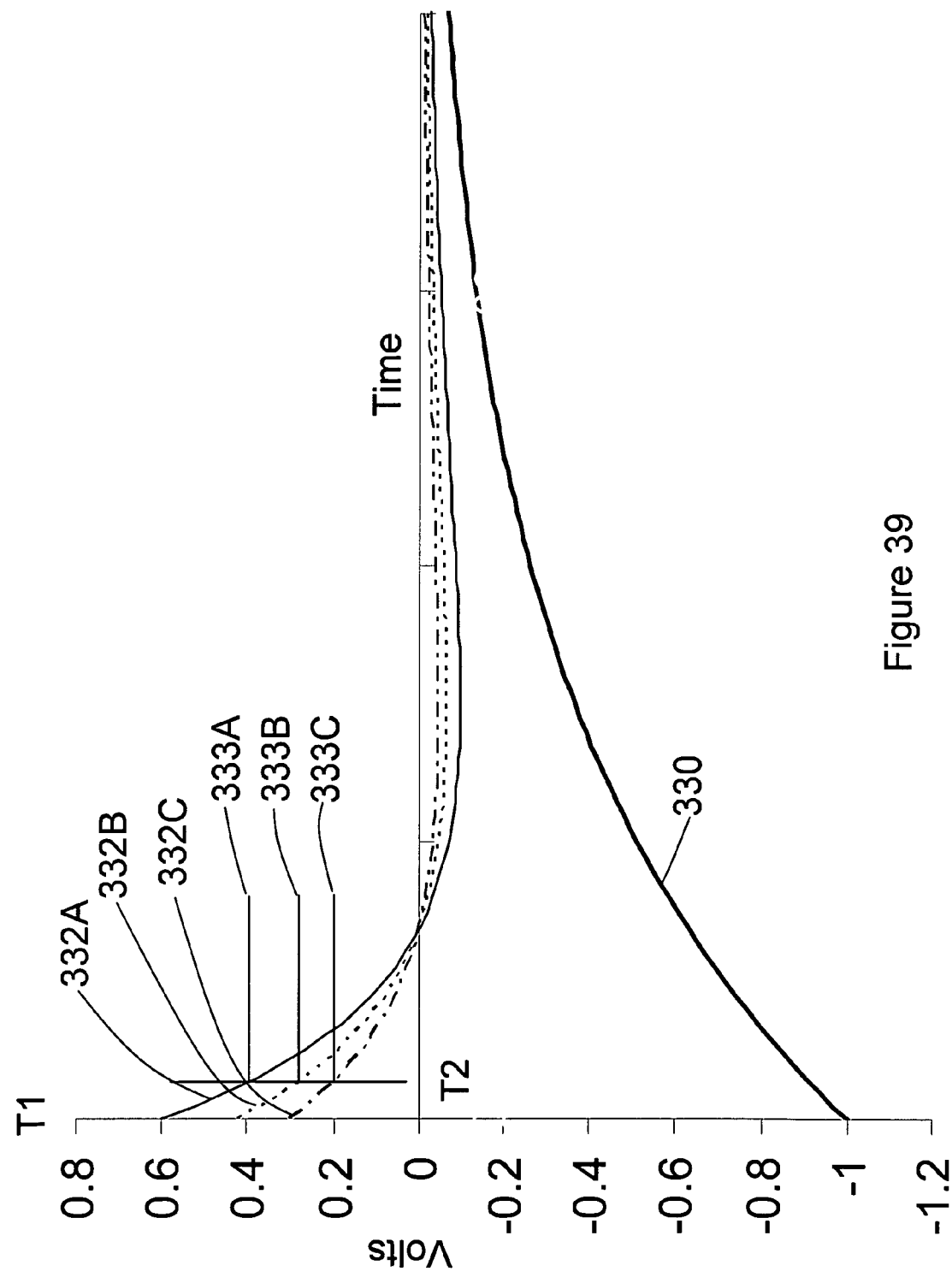
FIG. 39 illustrates voltage versus time curves across the input and output of the sensor inductors in response to the application of a pulse to one of the sensor inductors.

With a pulse is applied across terminal 310 and 312 from the pulse generator circuit 300, a decaying signal is generated across the terminals of the type illustrated in FIG. 39 by curve 330 having a maximum at the time of the application of the pulse and decaying to zero some time later depending upon the time constants of the circuit. The output of sensor inductor 316 with the armature 320 inserted at various locations, in response to the input pulse, is illustrated by curves 332A-332C. Curves 332A-332C illustrate the magnitude of the voltage from the output sensor inductor at different positions of the armature 320 relative to the sensor inductors, with 332A representing the least insertion while 332 B and 332C represent deeper insertions. Hence it can be seen that magnitude of the sensor output is a function of the position of the armature relative to sensor inductors. By selecting a time T2 to make measurements from the application of the pulse to the zero T1, a measurement can be made of the position of the armature relative to the sensor inductors from the instantaneous voltage levels 333A-333C.

The sensitivity of the sensor is quite high and the sensor inductors are essentially independent of resistance (or Q). Hence, with the Q insensitive sensor inductors as described herein, the size of the sensor can be designed to fit a wide variety of monitoring purposes without facing Q restrictions. This is particularly important when the sensor inductors are scaled in size for miniaturization.

FIG. 40 discloses a basic block diagram of the sensor inductors 402 of the invention in conjunction with the monitoring circuit electronics for monitoring the flux changes between the sensor inductors in response to the deformations of the surface under test. A pulse generator 400 applies electrical signals to the sensor inductors 402 via a connector 404. A monitor circuit 406 identifies the changes in the output of the sensor inductors 402 and provides digital signals to a microcontroller 408, which in turn analyzes the digital signals and provides an output indicative of the movements monitored to a display 410, a data storage unit 412, a data port and interface unit 414 an alarm 416 and a transceiver 418. An on-off and manual control circuit 420 is connected to the system control 422. The system control 422 also receives signal from the transceiver 418. The combination sensor-electronics unit of the type illustrated in FIG. 40 is contained within the dashed lines. The input to the monitoring system can be connected to the sensor inductors 402 via a quick connect-disconnect connector or terminals The monitoring system is adapted to be connected to external networks 428, a computer 430 such as a lap top computer, and an external transceiver 432. The computer 430, when connected, provides the human interface additional control means for the operation and read out of the monitoring system, stores data in long term memory, and translates the data for control, visual and/or audible indications and provides programming of the microcontroller 408.

For portable or ambulatory use, the unit 424 is powered by a power source using two 3.3 volts watch type batteries connected in series. The resulting 6.6 volt node is connected through a standard DC regulator circuit to maintain a constant 3.3V output. Two large capacitors (100 μF) are included in the power circuit, one between the 6.6 volt node and ground and the other between the 3.3V regulator output and ground for supplying high currents for short periods of time, such as could be needed, for example, to write data to the FLASH data storage. The regulator is gated so it does not supply power when hooked up to an exterior 3.3 volt source, such as supplied by the computer 430. To reduce the drain on the batteries, a separate timing arrangement is used to allow the monitoring circuit 406 and the microcontroller 408 to switch to a "sleep" mode of operation between data acquisition sets. On the other hand if portability is not important, then a fast transient response power supply having a capacitive output could be used. Further, it is preferred if the output impedance of the power supply is lower than the impedance of the sensor inductors, otherwise the impedance of the power supply would add to the sensor impedance resulting in a lower delay time. It is also preferred if the inductance of the power supply be negligible with respect to the inductance of the sensor inductors so that the power supply does not exhibit a voltage drop when applying a pulse to the sensor inductors.

Figure 41:
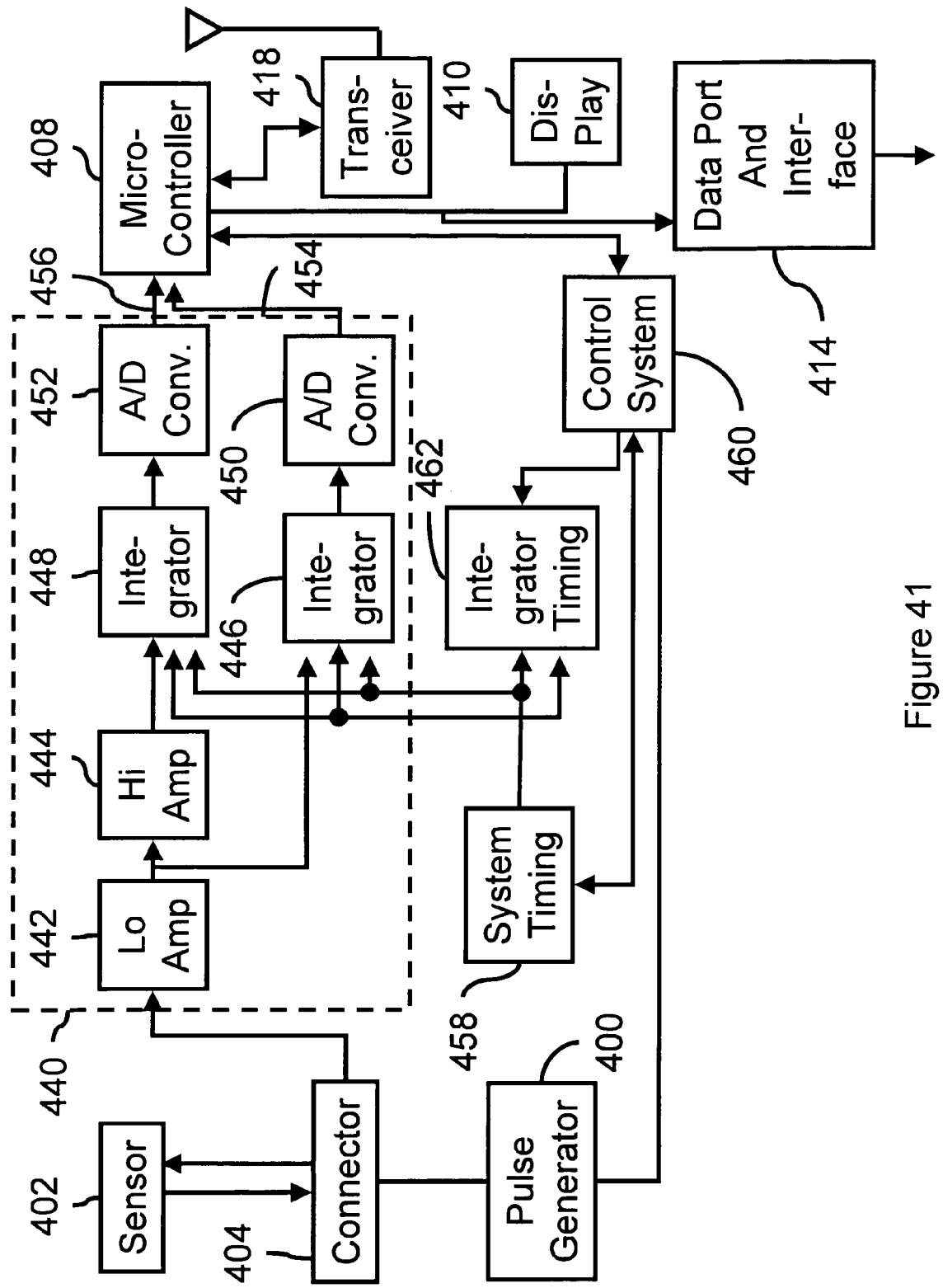
FIG. 41 is an expanded block diagram of a portion of the block diagram of FIG. 40.

The monitor circuit 406 is shown within the dashed block of FIG. 41. The monitor circuit analyzes the response and amplitude characteristics of the output signal from the sensor to provide indications of the movements or positioning of the sensor inductor and the armature. The monitor circuit includes a low gain amplifier 442 driving a high gain amplifier 444, the outputs of each are applied to separate analog memory circuits such as, for example, the integrator circuits 446 and 448, respectively for generating a reading over a time after the application of a pulse to the sensor 402 by the pulse generator 400 as controlled by the integrator timing circuit 462. Alternatively the microcontroller 408 can use a timing arrangement to measure the time between the application of the pulse and when the outputs of the A/D converters 450 and 452 indicate a predetermined amplitude level of the output signal. In addition the signals from the A/D converters can be integrated over the response time of the pulse since the response time remains constant and only the amplitude of the signal changes. The high and low gain amplifiers have inputs for placing the amplifier circuits in a standby low power mode of operation when the system is put in a power savings sleep mode of operation. The low gain amplifier 442, or the high gain amplifier 444, or both amplifiers, can have a variable gain feedback loop, manually or electronically operable, for adjusting the system sensitivity. The outputs of the integrator circuits 446 and 448 are applied to separate A/D converter circuits 450 and 452 respectively, each of which outputs digital signals to the microcontroller 408 via the low gain data line 454 and via the high gain data line 456. The circuits are preferably CMOS with inputs set high or low during periods of inactivity so as not to draw a significant amount of current. The microcontroller 408 analyzes the digital signals and sends an output indicative of sensor displacement to the data port and interface 414, display 410, and the transceiver 418. The system timing 458 includes a high frequency clock and the control system control circuit 460, the data acquisition functions of the monitor circuit 406, and the microcontroller 408. The operation of the integrator circuits 446 and 448 are controlled through the integrator timing circuit 462.

The low gain output 454 is used to provide a gross indication of the absolute displacement, while the high gain output 456 provides the high sensitivity output of the relative displacements, and in particular changes in the relative displacements with time. The relative displacement is important to infer changes in the larger system. For example, if the relative displacement of the sensor inductors indicated a change of 1%, and the sensor attach points are one inch apart, then this would infer a change of 0.4 inches.

In the embodiments of the system apparatus of the invention described above the microcontroller 408 outputs digital data indicative of the sensor inductors displacement to the computer 430, which can be, for example a standard lap top computer including a screen and an alarm for providing added visual and audible outputs. The computer 430 also provides a control signal that can be used for controlling the movements of the object being monitored. However it should be understood that the microcontroller 408 can be specifically tailored to function as a single piece of specialized monitoring equipment.

FIGS. 42A-42F illustrate the steps contained in software routines used in the system for the data collection, transmission, and reception, to and from the output-input devices of FIG. 40, including the network 428, the computer 430, and the transceiver 432.

With regards to FIGS. 42A-42C concerning the processing data from the sensor 402, the main routine 500 initializes two timers, timer 0 and timer 2, and enables their associated software interrupts 502. In step 504, timer 2 is set to a frequency, for example, of 4 Hz. The timer 2 ISR interrupt of step 520 occurs, for example, every 0.25 seconds, to periodically initiate a data collection operation. While waiting for the timer 2 interrupt, the system will remain at loop 506 with a slow clock speed of approximately 32 KHz to conserve battery power.

When the timer 2 ISR step 520 interrupt occurs, the clock speed is increased to an exemplary speed of 24 MHz for the data collection operation in step 522. In step 524, the low and high gain amplifiers 442 and 444 (FIG. 41) are turned on and the sensor 402 is pulsed during step 526 by the pulse generator 400. The integrator circuits 446 and 448 and the integrator circuit timing 462 are turned on by step 528, and the data signal from the sensor is stored for a time T1 by step 530, which is, for example, on the order of 1 microsecond. The integrator circuits are then turned off in step 532 and the sensor circuit 402 is reset during step 534. The clock speed is reduced, for example, to 6 MHz in step 536. In step 538, an A/D conversion routine is run on the stored data. The output-input devices are put in a transmit mode of operation by steps 540 and 541.

During the data transmission operation timer 2 interrupt is disabled in step 544 and the transmitter portion of the transceiver 418 is turned on in step 546. The timer 0 clock is set with a frequency, for example, on the order of 100 kHz and timer 0 interrupt is initiated during step 548. The timer 0 runs while timer 2 is disabled during the transmission mode of operation. The timer 2 interrupt sets the transceiver oscillator, for example, to 32 kHz during step 556. After the data is sent, timer 0 is disabled at step 552 and timer 2 is enabled during step 554 in preparation for the next data collection and transmission operation.

Figure 42F:
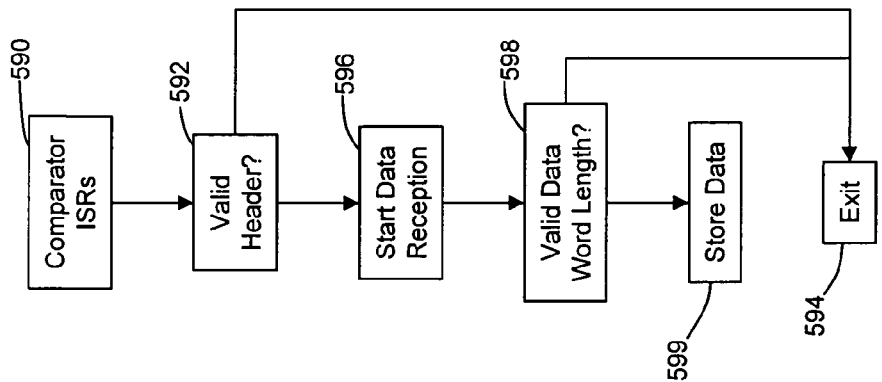
Figure 42E:
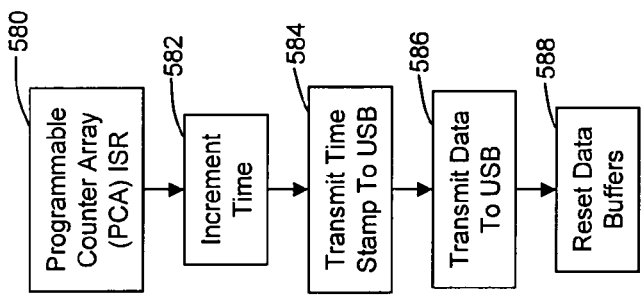
Figure 42D:
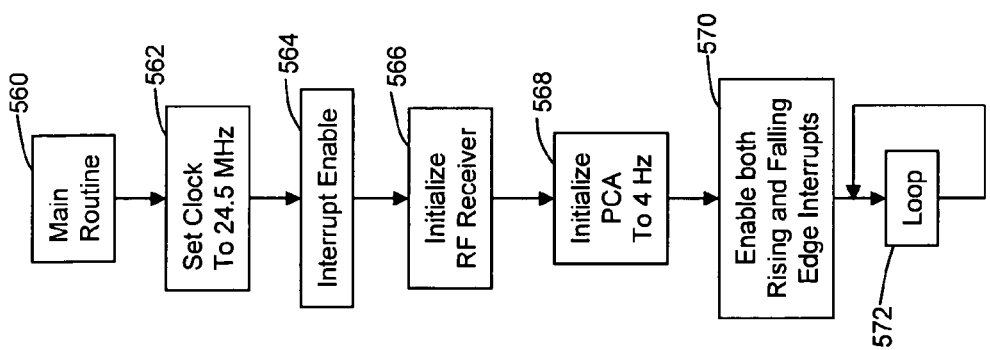

FIGS. 42D-42F illustrate the steps contained in software routines used to receive data. The main routine step 560 sets the clock to an exemplary speed of 24.5 MHz. Unlike the battery-powered sensor transmitter, the receiver hardware may not have power limitations and the clock speed can be optimized to a faster speed. In step 564, an interrupt is enabled to initialize, during step 566, the receiver portion of the transceiver 432 to monitor incoming data. A Programmable Counter Array (PCA) is initialized during step 568, for example, to 4 Hz. In step 570, the pulse rising and falling edge interrupts are enabled for monitoring the incoming data. The receiver will remain in the loop mode of step 572 until an interrupt from the PCA occurs.

The PCA in step 580 increments time in step 582 and a time stamp is provided to the USB in step 586 by the PCA interrupt ISR. The buffers are reset during step 588. The Comparator ISR routine of step 590 is used to test whether the incoming data packet is valid. If the data packet is identified with a valid header in step 592, the data reception will begin in step 596. The data packet is then tested for valid word length in step 598. If both tests are valid, the data is stored in the data buffers in step 599, otherwise, the data packet is abandoned and the system will exit in step 594 awaiting the next data packet.

After data transmission from the receiver to USB 586, the data buffers are reset in step 588.

The invention provides solutions for applications requiring the monitoring delicate items or flexible membrane, such as skin, with insignificant interference from the monitoring apparatus. By insignificant interference it is meant that the sensor, its size, its mass, its loose fitting parts (for longitudinal, rotation and wobble) and the flexible electrical connections thereto do not place restrictive forces on the portion or part of the membrane under test of a magnitude that would detrimentally impact the accuracy of the measurements.

The invention, as described in previous embodiments, may be attached to the human skin in a variety of positions and in multiple locations. In its miniaturized form the tiny, lightweight sensor does not require the cumbersome use of jackets or belts that inhibit freedom of movement and are uncomfortable for long periods of time. This invention permits sensitive surveillance in the micron range allowing monitoring for small changes in breathing patterns of a sleeping infant or adult while being barely perceptible the wearer.

The design of the sensor provides the capability of making sensors small in size allowing their placement on nearly all areas of the body such as the chest, abdomen, neck, back, and penis, legs, arms among others, allowing invention to be used for observing a wide variety of physiological symptoms.

Figure 43:
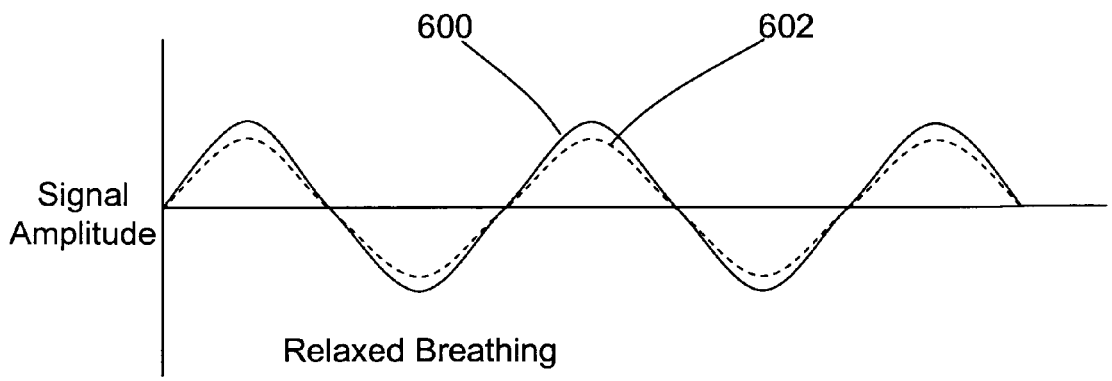
FIG. 43 is an illustration of the use of sensors to simultaneously monitor chest and abdominal relaxed breathing.
Figure 44:
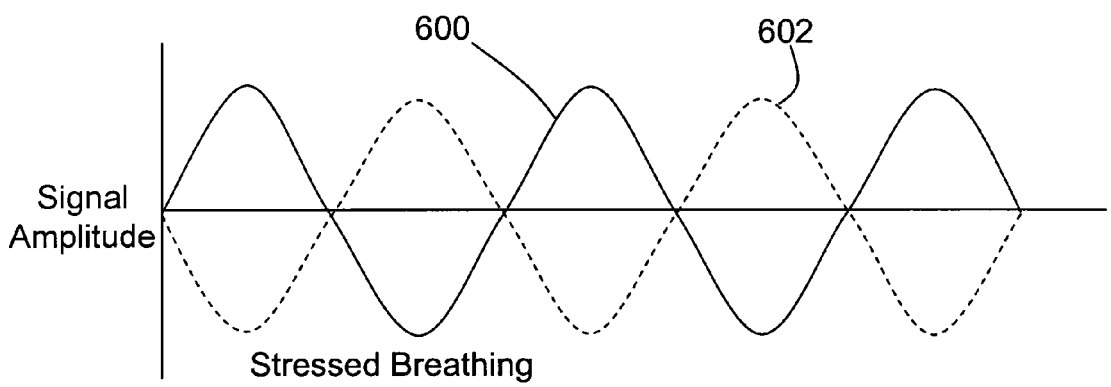
FIG. 44 is an illustration of the use of sensors to simultaneously monitor chest and abdominal stressed breathing.

FIGS. 43 and 44 are illustrations of the high gain output of the monitor system when the sensors are attached to monitor breathing. The line 600 depicts the output of a sensor system attached to abdomen to monitor abdominal breathing and the output 602 of a second sensor system attached to the chest to monitor chest breathing. During the relaxed breathing of FIG. 43, the outputs 600 have low amplitudes and are generally in phase. During the stressed breathing of FIG. 44, the magnitudes of the outputs 602 increase and are out of phase.

Additionally, a plurality of the sensors may be placed such that they cover a wide range of area on the human body as in the case of labor contractions in abdomen of a pregnant woman. Sensors may be place in various patterns on the abdomen to track deformations such as expansion and contraction of the skin in a topographical array to provide analysis of skin displacements which may occur in waves.

On the other hand, if monitoring massive objects, such as for example, automobile shock absorbers, where the sensor would be exposed to difficult environmental conditions, the loose mechanical fit may not be appropriate, requiring seals and sealed electrical connections, but so as not to interfere with the shock absorber operation. However, the sensor configuration, the excitation of the sensor inductor by pulses and the output signals, the monitoring circuits, systems, and method of the invention will apply to such rugged versions of the sensor of the invention.

The outputs of the coils 166 and 168 via connector 176 of the sensor arrangement of FIGS. 23-27 are illustrated in FIG. 45 as the excitation signal is applied to the coil 161. As the armature 170 including the coils 166 and 168 moves relative to the coil 161, the amplitude of the output signals from coils 166 and 168 as analyzed by the monitoring circuit has three zero points 606, 608, and 610 and also changes in polarity which provide the indication of the positional locations as well as movements.

Specific applications and exemplary embodiments of the invention have been illustrated and discussed, which provides a basis for practicing the invention in a variety of ways and in a variety of applications. Numerous variations are possible within the scope of the invention. Features and elements associated with one or more of the described embodiments are not to be construed as required elements for all embodiments. Other changes and modifications in the specifically described embodiments can be carried out without departing from the principals of the invention that is intended to be limited only by the scope of the appended claims.

What is claimed is:

1. A sensor system for monitoring bodily functions comprising at least one sensor having attachment unit to be attached to external body skin at two separate locations for providing indications of skin deformation between the two locations, wherein the sensor comprises two generally planar coils juxtapositioned with a spacing in between wherein one of the coils functions as an excitation coil and the other as the output coil, and one of the coils is adapted to be connected to the skin, a metallic shield positioned within the coil spacing being adapted to be attached to the skin, wherein the shield and the coils are movable with respect to each other to follow deformations of the skin between the attachments of the coil and shield to provide indications of movement in the form of changes of the amount of magnetic flux transmitted between the coils.

2. A sensor system as defined in claim 1 wherein the coil and shield are adapted to be attached to the skin locations external of the chest and wherein the indications provided by the sensor are a function of expansions and contractions of the chest.

3. A sensor system as defined in claim 1 wherein the sensor is adapted to be attached to the skin locations external of the abdomen and wherein the indications provided by the sensor are a function of expansions and contractions of the abdomen.

* * * * *